(12) United States Patent
Altel et al.

(10) Patent No.: US 12,269,821 B2
(45) Date of Patent: Apr. 8, 2025

(54) DISCOVERY OF NOVEL FIRST IN CLASS NATURE-INSPIRED COMPOUNDS TARGETING THE MITOCHONDRIAL FUNCTION AND PHARMACEUTICAL COMPOSITION THEREOF

(71) Applicant: University of Sharjah, Sharjah (AE)

(72) Inventors: Taleb H. Altel, Sharjah (AE); Vunnam Srinivasulu, Sharjah (AE); Saleh Ibrahim, Lubeck (DE); Paul Schilf, Lubeck (DE)

(73) Assignee: UNIVERISTY OF SHARJAH (AE)

( * ) Notice: Subject to any disclaimer, the term of this patent is extended or adjusted under 35 U.S.C. 154(b) by 821 days.

(21) Appl. No.: 17/263,751

(22) PCT Filed: Jul. 25, 2019

(86) PCT No.: PCT/IB2019/056362
§ 371 (c)(1),
(2) Date: Jan. 27, 2021

(87) PCT Pub. No.: WO2020/021489
PCT Pub. Date: Jan. 30, 2020

(65) Prior Publication Data
US 2021/0179605 A1    Jun. 17, 2021

Related U.S. Application Data

(60) Provisional application No. 62/711,401, filed on Jul. 27, 2018.

(51) Int. Cl.
*C07D 459/00* (2006.01)
*A61P 35/00* (2006.01)
*C07D 471/20* (2006.01)
*C07D 498/14* (2006.01)

(52) U.S. Cl.
CPC ............ *C07D 459/00* (2013.01); *A61P 35/00* (2018.01); *C07D 471/20* (2013.01); *C07D 498/14* (2013.01)

(58) Field of Classification Search
CPC .................................................. C07D 413/14
USPC .......................................................... 540/456
See application file for complete search history.

(56) References Cited

U.S. PATENT DOCUMENTS

| | | | |
|---|---|---|---|
| 7,582,619 B2 | 9/2009 | von Borstel | |
| 7,691,819 B2 | 4/2010 | Henry et al. | |
| 9,511,064 B2 | 12/2016 | Pohlmann et al. | |
| 2005/0272723 A1 | 12/2005 | Glick | |
| 2018/0044295 A1 | 2/2018 | Trushina et al. | |

FOREIGN PATENT DOCUMENTS

| | | |
|---|---|---|
| EP | 0202774 A2 | 11/1986 |
| EP | 0401929 A2 | 12/1990 |
| WO | 2014009222 A1 | 1/2014 |
| WO | 2017190038 A1 | 11/2017 |

OTHER PUBLICATIONS

Srinivasulu et al., Nature Communications (2018), 9(1), 1-14.*
Isidro-Llobet et al., "Diversity-oriented synthesis of macrocyclic peptidomimetics", PNAS, 2011, vol. 108, Issue 17, pp. 6793-6798, 6 pages.
Gaich & Baran, "Aiming for the Ideal Synthesis", The American Chemical Society, Journal of Organic Chemistry, 2010, vol. 75, pp. 4657-4673, 17 pages.
Green et al., "Bio-Inspired Domino oxa-Michael/Diels-Alder/oxa-Michael Dimerization of para-Quinols", Angew. Chem. International Edition, Edinburgh Research Explorer, 2018, vol. 57, Issue 21, pp. 6198-6202, 7 pages.
Mukai et al., "Bioinspired chemical synthesis of monomeric and dimeric stephacidin A congeners", Nat. Chem., 2018, vol. 10, Issue 1, pp. 38-44, 15 pages.
Cui et al., "Creation and manipulation of common functional groups en route to a skeletally diverse chemical library", PNAS, 2011, vol. 118, Issue 17, pp. 6763-6768, 6 pages.
Nie et al., "A Multidimensional Diversity-Oriented Synthesis Strategy for Structurally Diverse and Complex Macrocycles", Angew. Chem. International Edition, 2016, vol. 55, p. 11139-11143, 5 pages.
Aine et al., "Pharmacological Importance of Optically Active Tetrahydro-β-carbolines and Synthetic Approaches to Create the C1 Stereocenter", Molecules, 2014, vol. 19, pp. 1544-1567, 24 pages.
Sankar et al., "Stereoselective synthesis of a natural product inspired tetrahydroindolo[2,3-a]-quinolizine compound library", Elsevier, Bioorganic & Medicinal Chemistry, 2015, vol. 23, pp. 2614-2620, 7 pages.
Lebold et al., "A divergent approach to the synthesis of the yohimbinoid alkaloids venenatine and alstovenine", Nat. Chem., 2013, vol. 5, Issue 2, pp. 126-131, 14 pages.
Stork et al., "Regiospecific and Stereoselective Syntheses of (±)- and (−)-Reserpine", Journal of American Chem. Society, 2005, vol. 127, Issue 46, pp. 16255-16262, 15 pages.
Nemoto et al., "Catalytic Asymmetric Total Synthesis of Tangutorine", American Chemical Society, 2010, vol. 12, Issue 4, pp. 872-875, 20 pages.
Arioli et al., "Stereoselective Total Synthesis of the Putative Structure of Nitraraine", Journal of Organic Chem., 2014, vol. 79, Issue 16, pp. 7740-7745, 18 pages.
Ye et al., "Therapeutic Potential of Spirooxindoles as Antiviral Agents", ACS Infect. Dis., 2016, vol. 2, Issue 6, pp. 382-392, 24 pages.
Cui et al., "Novel Mammalian Cell Cycle Inhibitors, Tryprostatins A, B and Other Diketopiperazines Produced by Asperfillus fumigatus", The Journal of Antibiotics, 1996, vol. 49, Issue 6, pp. 527-533, 7 pages.

(Continued)

*Primary Examiner* — Niloofar Rahmani
(74) *Attorney, Agent, or Firm* — MH2 Technology Law Group, LLP

(57) ABSTRACT

The present invention relates to novel antitumor agents and pharmaceutically acceptable salts thereof, processes and intermediates for the manufacture of these novel constrained cyclic frameworks of general formula I and II, and medicaments containing such compounds.

12 Claims, 2 Drawing Sheets

(56) References Cited

OTHER PUBLICATIONS

Weinberg & Chandel, "Targeting mitochondria metabolism for cancer therapy", Nature Chemical Biology, 2015, vol. 11, Issue 1, 18 pages.

Porporato et al., "Mitochondrial metabolism and cancer", Cell Research, 2018, vol. 28, pp. 265-280, 16 pages.

Ward & Thompson, "Metabolic Reprogramming: A Cancer Hallmark Even Warburg Did Not Anticipate", Cancer Cell, 2012, vol. 21, Issue 3, pp. 297-308, 30 pages.

Andreux et al., "A method to identify and validate mitochondrial modulators using mammalian cells and the worm *C. elegans*", Scientific Reports, 2014, vol. 4, Article No. 5285, 10 pages.

Wagner et al., "Large-scale chemical dissection of mitochondrial function", Nat Biotechnol., 2008, vol. 26, Issue 3, pp. 343-351, 30 pages.

Srinivasulu et al., "Multidirectional desymmetrization of pluripotent building block en route to diastereoselective synthesis of complex nature-inspired scaffolds", Nature Communications, 2018, vol. 9, Article 4989, 14 pages.

Godfraind et al., "Effects of yohimbine, rauwolscine and corynanthine on contractions and calcium fluxes induced by depolarization and prostaglandin F2a in rat aorta", British Journal of Pharmacology, 1983, vol. 80, Issue 1, pp. 115-121, 7 pages.

Deka et al., "Biochemical Studies and Virtual Screening of Phytochemical Reservoir from Northeastern Indian Plants to Identify Anti-Cancer Agents", Journal of Biologically Active Products from Nature, 2018, vol. 8, Issue 2, pp. 104-124, 22 pages.

O'Connor & Maresh, "Chemistry and biology of monoterpene indole alkaloid biosynthesis", Natural Product Reports, 2006, vol. 23, pp. 532-547, 16 pages.

Wang et al., "Construction of Chiral Tetrahydro-β-Carbolines through Asymmetric Pictet-Spengler Reaction of Indolyl Dihydropyridines", Angewandte Chemie International Edition, 2017, vol. 56, 6 pages.

Luo et al., "A Fast Assembly of Pentacyclic Benz[f]indolo[2,3-a]quinolizidine Core by Tandem Intermolecular Formal Aza-[3 + 3] Cycloaddition/Pictet-Spengler Cyclization: A Formal Synthesis of (+/−)Tangutorine", Journal Organic Chemistry, 2004, vol. 69, pp. 4548-4550, 3 pages.

Salame et al., "Biomimetic Synthesis of Tangutorine Following New Biogenetic Proposals", Organic Letters, 2009, vol. 11, Issue 9, pp. 1891-1894, 4 pages.

Yu et al., "Spirooxindoles: Promising scaffolds for anticancer agents", European Journal of Medicinal Chemistry, 2015, vol. 97, Issue 5, pp. 673-698, 26 pages.

Chen et al., "Design, Synthesis, and Biological Activities of Spirooxindoles Containing Acylhydrazone Fragment Derivatives Based on the Biosynthesis of Alkaloids Derived from Tryptophan", Journal of Agric. Food Chem., 2016, vol. 64, Issue 34, pp. 6508-6516, 27 pages.

Lunt & Vander Heiden, "Aerobic glycolysis: meeting the metabolic requirements of cell proliferation", Annual Review Cell. Dev Biol., 2011, vol. 27, pp. 441-464, 27 pages.

Wallace et al., "Mitochondrial off targets of drug therapy", journal, 2008, vol. 29, Trends Pharmacol Science, pp. 361-366, 6 pages.

\* cited by examiner

DISCOVERY OF NOVEL FIRST IN CLASS NATURE-INSPIRED COMPOUNDS TARGETING THE MITOCHONDRIAL FUNCTION AND PHARMACEUTICAL COMPOSITION THEREOF

CROSS-REFERENCE TO RELATED APPLICATIONS AND PRIORITY

This patent application claims priority from PCT Patent Application No. PCT/IB2019/056362 filed Jul. 25, 2019, which claims priority from U.S. Provisional Patent Application No. 62/711,401 filed Jul. 27, 2018. Each of these patent applications are herein incorporated by reference in their entirety.

FIELD OF THE INVENTION

The present invention relates to novel antitumor agents and pharmaceutically acceptable salts thereof, processes and intermediates for the manufacture of these novel constrained cyclic frameworks as defined in the specification of general formula I and II, and medicaments containing such compounds. This invention also concerns the use of such compounds to modulate the cellular mitochondrial functions by measuring the ATP content, the mitochondrial membrane potential and the cellular redox potential as well as their toxicities and effects on T and B cells.

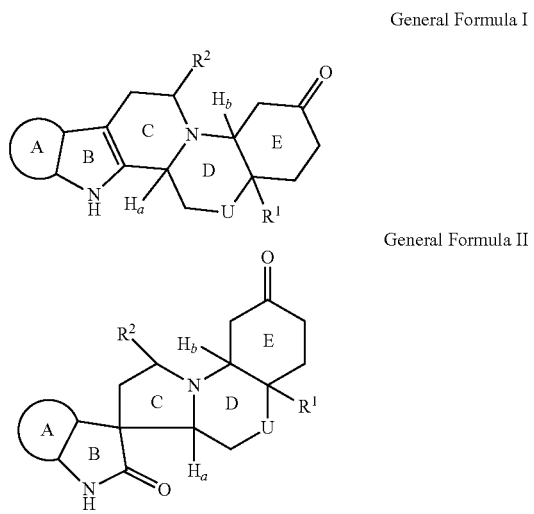

General Formula I

General Formula II

BACKGROUND OF THE INVENTION

Prior Art

Natural product estate represents a wealth of structural diversity with high 3D-content; however, there are well-documented difficulties linked to their use in screening experiments including their availability for clinical trials and SAR development (A. Isidro-Llobet et al., Diversity-oriented synthesis of macrocyclic peptidomimetics, *Proc. Natl. Acad. Sci., USA,* 2011, 108, 6793; T. Gaich et al., Aiming for the Ideal Synthesis, *J. Org. Chem.,* 2010, 75, 4657). Thus the recent decade or so has witnessed an upsurge in the development of privileged substructure diversity-oriented synthesis strategies for the de novo construction of nature-inspired compounds needed for phenotypic screening campaigns (N. J. Green et al., Bio-inspired Domino oxa-Michael/Diels-Alder/oxa-Michael Dimerization of para-Quinols, *Angew. Chem. Int. Ed,* 2018, 57, 6198; K. Mukai et al., Bioinspired chemical synthesis of monomeric and dimeric stephacidin A congeners, *Nat. Chem.,* 2018, 10, 38). One such strategy represents the use of a single pluripotent functional group that can be decorated through reactions with a variety of reagents, thereby empowering the synthesis of skeletally diverse compound collections with high 3D-content (J. Cui et al., Creation and manipulation of common functional groups en route to a skeletally diverse chemical library, *Proc. Natl. Acad. Sci, USA.* 2011, 108, 6763). Currently, there is growing consensus that, increasing the 3D-content and the number of stereocenters within specific library has been suggested to enhance the selectivity and potency toward a given target, hence increases the hit to lead success rate across several targets from a single library (F. Nie, A Multidimensional Diversity-Oriented Synthesis Strategy for Structurally Diverse and Complex Macrocycles, *Angew. Chem. Int. Ed. Engl.,* 2016, 55, 11139).

To this end, one of the important classes of natural products with high 3D-content, is the octahydroindolo[2,3-a]quinolizine monoterpene indole alkaloids, comprised of more than 2000 members and among the most studied natural product classes owing to their diverse biological activities and synthetic potential associated with these scaffolds (S. E. O'Connor et al., Chemistry and biology of monoterpene indole alkaloid biosynthesis. *Nat. Prod. Rep.,* 2006, 23, 532; A. E. Laine et al., Pharmacological importance of optically active tetrahydro-β-carbolines and synthetic approaches to create the C1 stereocenter, *Molecules,* 2014, 19, 1544). This molecular framework is produced by an array of plants and microorganisms. Several members of this monoterpene family possess biological activities useful for the treatment of many disease states (S. E. O'Connor et al., Chemistry and biology of monoterpene indole alkaloid biosynthesis. *Nat. Prod. Rep.,* 2006, 23, 532; M. G. Sankar et al., Stereoselective synthesis of a natural product inspired tetrahydroindolo[2,3-a]-quinolizine compound library. *Bioorg. Med Chem.* 2015, 23, 2614). Despite the existence of various multi-step stereoselective methods, direct access to diverse variants of these systems in a completely diastereo-controlled, step-economic, and atom-economic manner would be a remarkable achievement. In this context, Sarpong and Stork reported innovative approaches for the synthesis of various scaffolds of this class of natural products (T. P. Lebold et al., A divergent approach to the synthesis of the yohimbinoid alkaloids venenatine and alstovenine, *Nat. Chem.,* 2013, 5, 126; G. Stork et al., Regiospecific and Stereoselective Syntheses of (±)-Reserpine and (−)-Reserpine, *J. Am. Chem. Soc.,* 2005, 127, 16255). Furthermore, Shu-Li You (S. G. Wang et al., Construction of Chiral Tetrahydro-β-Carbolines: Asymmetric Pictet-Spengler Reaction of Indolyl Dihydropyridines, *Angew. Chem. Int. Ed.,* 2017, 56, 7440) and Hongbin Zhai (S. Luo et al., A Fast Assembly of Pentacyclic Benz[f]indolo[2,3-a]quinolizidine Core by Tandem Intermolecular Formal Aza-[3+3] Cycloaddition/Pictet-Spengler Cyclization: A Formal Synthesis of (±)-Tangutorine, *J. Org. Chem.,* 2004, 69, 4548) described elegant synthesis of these scaffolds employing variants of Pictet-Spengler reaction. Additionally, important contributions to access this class of natural products were also reported by Yasumasa Hamada (T. Nemoto et al., Catalytic Asymmetric Total Synthesis of Tangutorine, *Org. Lett.,* 2010, 12, 872), Erwan Poupon, (R. Salame et al., Biomimetic Synthesis of Tangutorine Following New Biogenetic Proposals, *Org. Lett.*, 2009, 11, 1891) and Mercedes Amat, (F. Arioli et al., Stereoselective Total Synthesis of the Putative Structure of Nitraraine, *J. Org. Chem.*, 2014, 79, 7740). Despite the importance of these stepwise stereoselective methods, a general and modular strategy for the preparation of various analogues of the octahydroindolo[2,3-a]quinolizine monoterpene indole alkaloids family is highly desirable.

In addition, spiro-oxindole scaffolds represent the basic framework of a wide range of natural products and biologically significant compounds, including antiviral (N. Ye et al., Therapeutic Potential of Spirooxindoles as Antiviral Agents. *ACS Infect. Dis.* 2016, 2, 382), anticancer (B. Yu et al., Spirooxindoles: Promising scaffolds for anticancer agents. *Eur. J. Med. Chem.* 2015, 97, 673) activities as well as cell cycle inhibitors (C. B. Cui et al., Novel mammalian cell cycle inhibitors, spirotryprostatins A and B, produced by *Aspergillus fumigatus*, which inhibit mammalian cell cycle at G2/M phase. *Tetrahedron*, 1996, 52, 12651). For example, a natural product spirotryptostatin, showed a promising anticancer activity (L. Chen et al., Design, Synthesis, and Biological Activities of Spirooxindoles Containing Acylhydrazone Fragment Derivatives Based on the Biosynthesis of Alkaloids Derived from Tryptophan. *J. Agric. Food Chem.* 2016, 64, 6508).

On the other hand, targeting the mitochondrial function has been implemented as a potential anticancer approach by depriving cancer cells from a main energy source (S. E. Weinberg et al., Targeting mitochondria metabolism for cancer therapy, *Nat. Chem. Biol.*, 2015, 11, 9; P. E. Porporato, et al., Mitochondrial metabolism and cancer, *Cell Res.*, 2018, 28, 265) Limiting the mitochondrial energy production affects the availability of ATP in cancer cells and so the biosynthesis of macromolecules and the cell signaling required for tumor growth (P. S. Ward et al., Metabolic reprogramming: a cancer hallmark even warburg did not anticipate, Cancer cell, 2012, 21, 297; S. Y. Lunt et al., Aerobic glycolysis: meeting the metabolic requirements of cell proliferation, *Annu. Rev. Cell. Dev. Biol.*, 2011, 27, 441). While several approaches to identify modulators of mitochondrial functions have been developed they mostly rely on screening of widely known chemical structures and agents (P. A. Andreux, et al., A method to identify and validate mitochondrial modulators using mammalian cells and the worm *C. elegans. Sci. Rep.*, 2014, 4, 5285; B. K. Wagner et al., Large-scale chemical dissection of mitochondrial function, *Nat. Biotechnol.*, 2008, 26, 343; K. B. Wallace et al., Mitochondrial off targets of drug therapy, *Trends Pharmacol Sci.*, 2008, 29, 361). The approach presented here aims to evaluate and develop novel chemical structures with enhanced effects on mitochondrial and cellular functions to modulate the cellular metabolism to tackle cancer cells proliferation and survival. The present invention introduces a one-pot practical and modular approaches to access diversely functionalized novel heterocyclic systems with more than three contiguous chiral centers and broad distribution of molecular shapes via desymmetrization of the oxidative dearomatization products of phenols following a formal Pictet-Spingler/Aza-Michael addition cascade. These novel heterocyclic systems were further transformed into spiro-oxindole systems in one step manner.

SUMMARY OF THE INVENTION

The present invention relates to compounds of general formula I and II, processes for their preparation, intermediates, stereoisomers, and the use of such novel compounds for different disease states including but not limited to, cell proliferative diseases and any diseases that are connected to the modulation of cellular metabolism and mitochondrial function.

Compounds of General Formula I

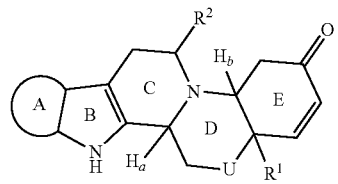

Wherein,

denotes a phenyl ring which may be unsubstituted or substituted with 1, 2, 3 or 4 substituents independently selected from a halogen atom, CN, $R^3$, $OR^3$, $SR^3$, $N(R^3)_2$, $C(O)R^3$, $C(O)OR^3$, $NR^3C(O)R^3$, $C(O)NR^3$, $SO_2R^3$, $NR^3SO_2R^3$, $SO_2N(R^3)_2$.

U denotes —$CH_2$ or —O.

$R^1$ denotes halogen atom, $R^3$, $OR^3$, $SR^3$, $N(R^3)_2$, $NR^3C(O)R^3$, $C(O)NR^3$, $SO_2R^3$, $NR^3SO_2R^3$, $SO_2N(R^3)_2$.

$R^2$ denotes hydrogen, halogen atom, CN, $R^3$, $OR^3$, $SR^3$, $N(R^3)_2$, $C(O)R^3$, $C(O)OR^3$, $NR^3C(O)R^3$, $C(O)NR^3$, $SO_2R^3$, $NR^3SO_2R^3$, $SO_2N(R^3)_2$, $CH_2C(O)R^3$, $CH_2C(O)OR^3$, $CH_2NR^3C(O)R^3$, $CH_2C(O)NR^3$, $CH_2SO_2R^3$, $CH_2NR^3SO_2R^3$, $CH_2SO_2N(R^3)_2$.

$R^3$ is independently hydrogen or an optionally substituted group selected from a $C_{1-6}$ aliphatic group, a monocyclic 3-8 membered saturated, partially unsaturated, or aryl ring having 0-4 heteroatoms independently selected from nitrogen, oxygen, or sulfur, or a bicyclic 8-10 membered saturated, partially unsaturated, or aryl ring having 0-5 heteroatoms independently selected from nitrogen, oxygen, or sulfur.

In another embodiment, $R^3$ is selected from the group consisting of: —$CX_3$, —$CHX_2$, and —$CH_2X$, wherein X is chlorine, fluorine, bromine, or iodine.

The stereochemical relation between $H_a$, $H_b$, $R^1$ and $R^2$ is either in the form of pure enantiomers, diastereoisomers or racemic mixtures.

In one embodiment, $R^1$ is connected to its vicinal quaternary carbon in the ring E to form an alicyclic ring.

In another embodiment, $R^1$ is connected to its vicinal secondary carbon in the ring E to form an alicyclic ring.

In yet another embodiment, present invention provides a process for the preparation of compound of general formula I, the process comprising the steps of:

i. Reacting a compound of formula III

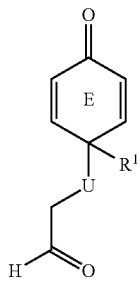

wherein W and U are as defined above in the general formula I with compound of formula IV

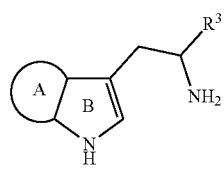

in the presence of TFA in a ratio ranging between 1:1 to 1:2 in a suitable aprotic solvent at a temperature in the range of −100° C. to rt for a period in the range of 2 to 12 h to obtain the compound of general formula V.

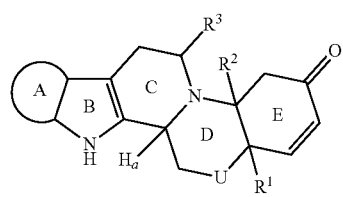

ii. Reacting a compound of general formula V with Pd/C in any suitable solvent under the hydrogen atmosphere at rt for a period in the range of 0.5 to 6 h to obtain compound of general formula I

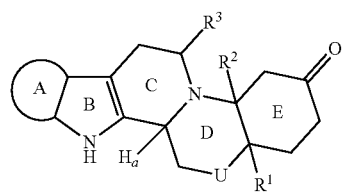

Compounds of General Formula II

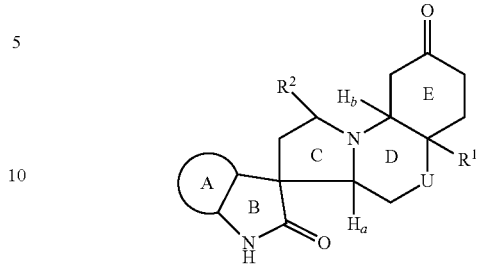

Wherein, (A)

U, $R^1$ and $R^2$ are defined as above in the general formula I

In another embodiment, present invention provides a process for the preparation of compound of general formula II, which comprises of:

Reacting a compound of general formula I with NBS in a ratio ranging between 1:1 to 1:2 in THF:AcOH:$H_2O$ (1:1:1) at a temperature in the range of 0° C. to 50° C. for a period in the range of 1 to 6 h to obtain a compound of general formula II.

In yet another embodiment, present invention provides a process for the preparation of compound of general formula VI, which comprises of:

Reacting a compound of general formula V with NBS in a ratio ranging between 1:1 to 1:2 in THF:AcOH:$H_2O$ (1:1:1) at a temperature in the range of 0° C. to 50° C. for a period in the range of 1 to 6 h to obtain a compound of general formula VI.

General formula VI

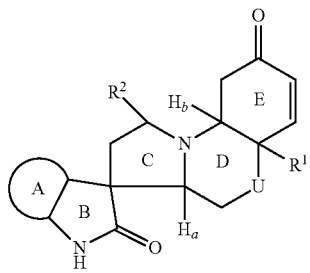

Necessary starting materials for the preparation of compounds of general formula III and IV may be obtained by standard procedures of organic chemistry and some of them are commercially available. In addition, they are obtainable by analogous procedures to those illustrated which are within the ordinary skill of an organic chemist.

In an even further embodiment, the invention also provides pharmaceutical compositions comprising compounds of general formula I, II, V and VI.

In another aspect, the present invention provides a method of treating cancer by administering an effective amount of a compound or pharmaceutical composition of this invention.

In yet another aspect, the present invention provides a method to analyze the cellular ATP content in a biological system by administering to the subject or contacting the biological system with an effective amount of a compound of invention.

In yet another aspect, the present invention describes a method to analyze the mitochondrial membrane potential in a biological system by administering to the subject or contacting the biological system with an effective amount of a compound of invention.

In yet another aspect, the present invention describes a method to analyze the cellular redox potential in a biological system by administering to the subject or contacting the biological system with an effective amount of a compound of invention.

DETAILED DESCRIPTION OF THE INVENTION

Diagram illustrating the method of preparation of compounds of formula I and V according to the invention are shown below.

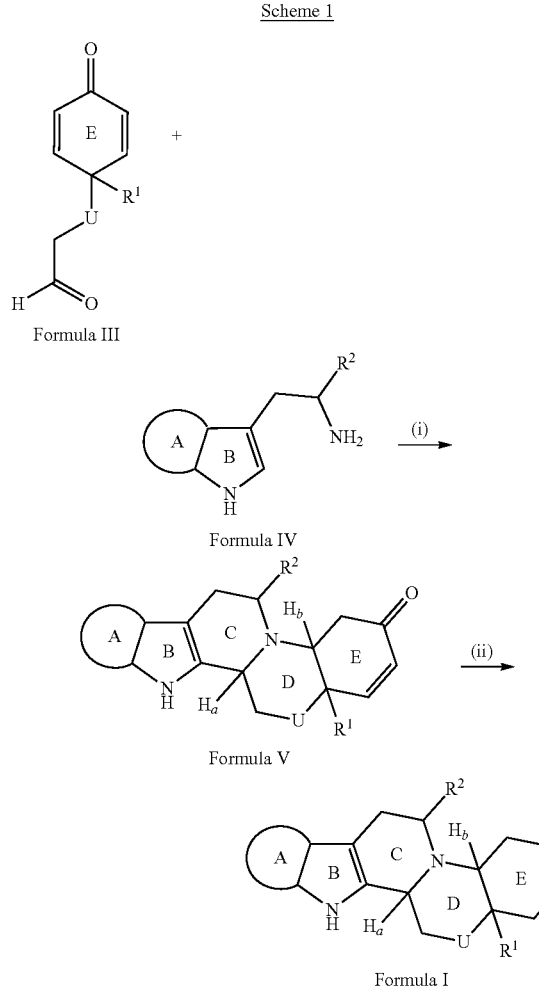

Reagents & Conditions: (i) TFA, DCM, -78° C. to rt; (ii) Pd-C/H2, MeOH:DCM (4:1), rt Diagrams illustrating the method of preparation of compound of formula II and VI according to the invention are shown below.

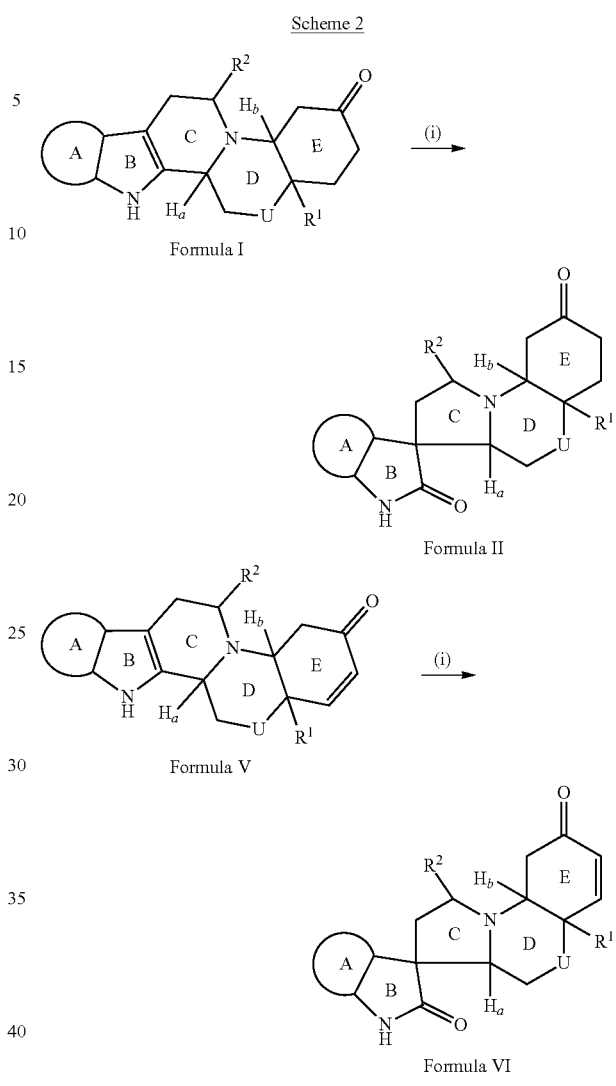

Reagents & Conditions: (i) NBS, TFA:AcOH:H₂O (1:1:1), -10° C. to rt, 1-2 h

DEFINITIONS

Figure 1:
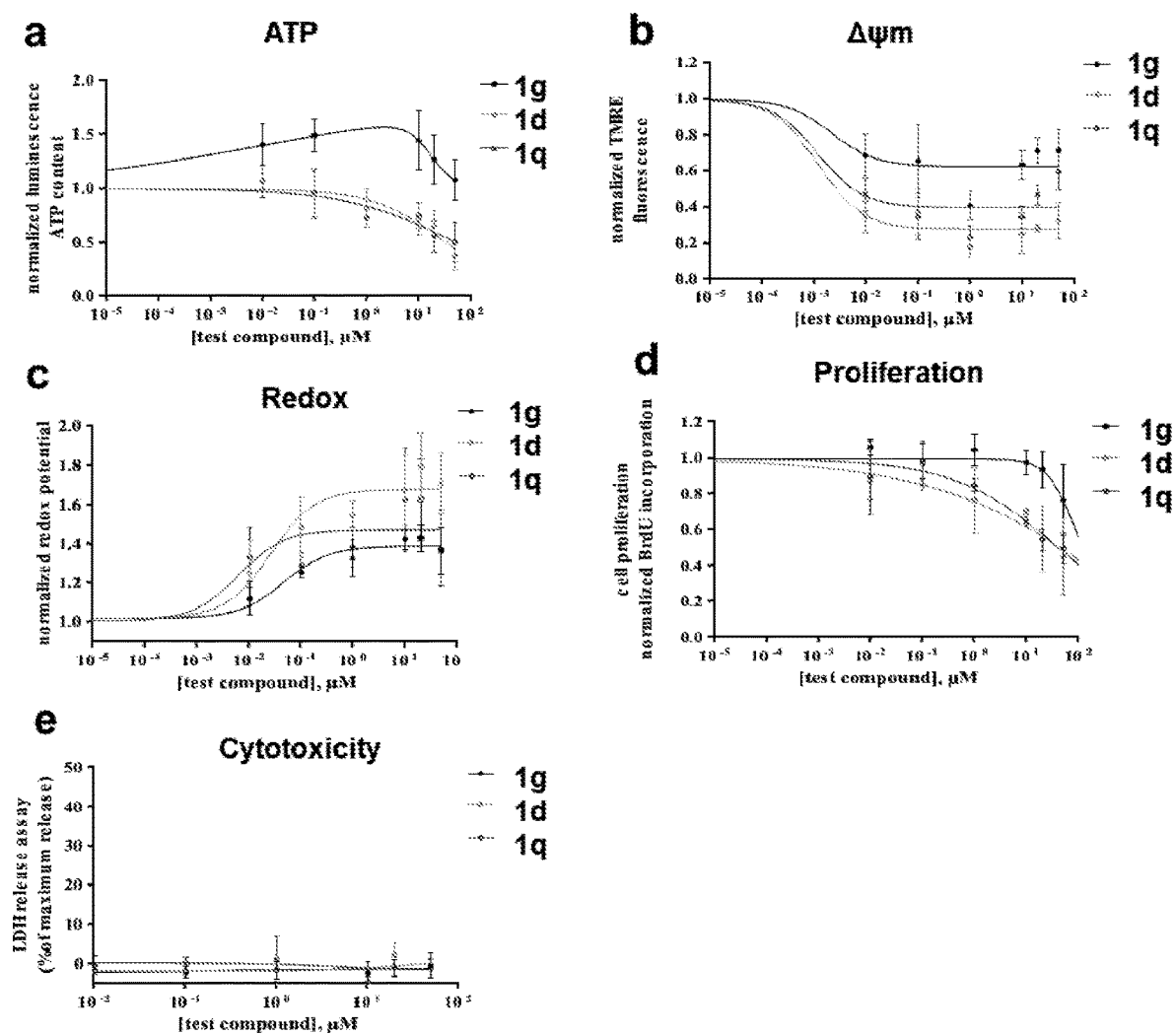
FIG. 1 Screening of a pilot library on cellular functions in Hepa1-6. a Effect of compounds 1d and 1q on ATP. b Effect of compounds 1d and 1q on mitochondrial membrane potential. c Effect of compounds 1d and 1 q on cellular redox potential. d Effect of compounds 1d and 1 q on cellular proliferation. e Cytotoxicity of compounds 1d and 1q. Error bars indicate standard deviation based on three replicated calculations. Significance was tested using an ANOVA test, with Dunnett's multiple comparison test.

The present invention relates to a novel process for the preparation of compounds of general formula I, II, V and VI, when discussing such compounds and their applications the following terms have the following meaning unless otherwise indicated.

The term "aryl" means an aromatic, or partially aromatic hydrocarbon group containing 6 to 10 carbon atoms and consisting of one or two rings which may be fused to each other or attached to each other via a single bond. Examples are phenyl, napthyl, biphenyl or indenyl.

The term "heteroaryl", as used herein, means an aromatic or partially aromatic group consisting of one or two rings, which may be fused to each other or attached to each other via a single bond, and containing 5 to 10 ring atoms wherein up to four, preferably one, two or three ring atoms are heteroatom(s) and the remaining ring atoms are carbon. Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

The term "alicyclic" means a saturated or unsaturated aliphatic cyclic ring system consisting of one or more rings, which may be fused to each other or attached to each other via a single bond, and containing 5 to 10 ring atoms more preferably carbons. Examples are cyclopentane, cyclohexane, cycloheptane, cyclooctane, terpene.

The term "alkyl", as used herein, denotes a saturated, linear- or branched chain hydrocarbon group containing 1 to 8, preferably 1 to 6, more preferably 1 to 4 carbon atoms, for example methyl, ethyl, propyl, isopropyl, 1-butyl, 2-butyl, tert-butyl and the like. Preferred "C1-C8 alkyl" groups have 1, 2 or 3 carbon atoms.

The term "halogen" means fluorine, chlorine, bromine or iodine.

The term "substituted" means a group which may be substituted one to three times by halogen atom, CN, $R^3$, $OR^3$, $SR^3$, $N(R^3)_2$, $C(O)R^3$, $C(O)OR^3$, $NR^3C(O)R^3$, $C(O)NR^3$, $SO_2R^3$, $NR^3SO_2R^3$, $SO_2N(R^3)_2$. With reference to substituents, the term "independently" means that when more than one of such substituents is possible, such substituents may be the same or different from each other.

The term "pharmaceutically acceptable salt" refers to conventional acid-addition salts or base-addition salts that retain the biological effectiveness and properties of the compounds of formula I, II, V and VI and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide.

The compounds of the invention can possess one or more asymmetric carbon atoms and are thus capable of existing in the form of optical isomers as well as in the form of racemic or non-racemic mixtures thereof. The compounds of the invention can be utilized in the present invention as a single isomer or as a mixture of stereochemical isomeric forms. Diastereoisomers, i.e., non superimposable stereochemical isomers, can be separated by conventional means such as chromatography, distillation, crystallization or sublimation. The optical isomers can be obtained by resolution of the racemic mixtures according to conventional processes, for example by formation of diastereoisomeric salts by treatment with an optically active acid or base. Examples of appropriate acids include, without limitation, tartaric, diacetyltartaric, dibenzoyltartaric, ditoluoyltartaric and camphorsulfonic acid. The mixture of diastereomers can be separated by crystallization followed by liberation of the optically active bases from these salts. An alternative process for separation of optical isomers includes the use of a chiral chromatography column optimally chosen to maximize the separation of the enantiomers.

The present invention also relates to the use of those active ingredients in the preparation of medicaments. In general, compounds of formula I, II, V and VI are administered either individually, or in combination with any other desired therapeutic agent, using the known and acceptable methods. Such therapeutically useful agents may be administered, for example, by one of the following routes: orally, for example in the form of dragees, coated tablets, pills, semi-solid substances, soft or hard capsules, solutions, emulsions or suspensions; parenterally, for example in the form of an injectable solution; rectally in the form of suppositories; by inhalation, for example in the form of a powder formulation or a spray; trans-dermal or intranasally. For the preparation of such tablets, pills, semi-solid substances, coated tablets, dragees and hard gelatine capsules, the therapeutically usable product may be mixed with pharmacologically inert, inorganic or organic pharmaceutical carrier substances, for example with lactose, sucrose, glucose, gelatine, malt, silica gel, starch or derivatives thereof, talcum, stearic acid or salts thereof, skimmed milk powder, and the like. For the preparation of soft capsules, pharmaceutical carrier substances such as, for example, vegetable oils, petroleum, animal or synthetic oils, wax, fat and polyols may be used. For the preparation of liquid solutions and syrups, pharmaceutical carrier substances such as, for example, water, alcohols, aqueous saline solution, aqueous dextrose, polyols, glycerol, vegetable oils, petroleum and animal or synthetic oils may be used. For suppositories, pharmaceutical carrier substances such as, for example, vegetable oils, petroleum, animal or synthetic oils, wax, fat and polyols may be used. For aerosol formulations, compressed gases that are suitable for this purpose, such as, for example, oxygen, nitrogen and carbon dioxide may be used. The pharmaceutically acceptable agents may also comprise additives for preserving and stabilizing, emulsifiers, sweeteners, flavourings, salts for altering the osmotic pressure, buffers, encapsulation additives and antioxidants.

The term "cancer" refers to a group of diseases involving abnormal cell growth with the potential to invade or spread to other parts of the body.

The term "anticancer" defines the use of natural/synthetic methods/substances for effective health care that contribute to/prevent the uncontrolled proliferation of tumor cells.

The term "proliferative" or "proliferation" in biological conditions points un-controlled multiplication because of failure in of normal functions of a system or even a cell in the context of present invention.

The term "drug" refers to a natural or synthetic substance which (when taken into a living body) affects its functioning or structure, and is used in the diagnosis, mitigation, treatment, or prevention of a disease or relief of discomfort.

The term "effective amount" when used in connection with a compound of general formula I, II, V and VI means an amount of the subject compound effective for treating or preventing cancer or any other diseases.

The word "mitochondria" coins to an organelle present mainly in eukaryotic organism that often refers to the metabolic center for life activities of a cell and provides energy for the cell.

As used herein, the following abbreviations have the below meanings.

rt=Room temperature
TFA=Trifluroacetic acid
NBS=N-bromosuccinamide
$Na_2SO_4$=Sodium sulfate
EtOAc=Ethylacetate
DCM=Dicholoromethane
MeOH=Methanol
THF=Tetrahydrofuran
AcOH=Acetic acid
NMR=Nuclear magnetic resonance
HRMS=High resolution mass spectroscopy
LCMS=Liquid chromatography-mass spectroscopy
ESI-TOF=Electrosprayionization-time of flight
h=hours
ATP=Adenosine Tri-Phosphate
Pd/C=Palladium-Carbon General Material and Methods Chemistry Chemical reagents and anhydrous solvents were purchased from Sigma-Aldrich and were used without further purification. Solvents for extraction and column chromatography were distilled prior to use. TLC analysis was performed with silica gel plates (0.25 mm, E. Merck, 60 $F_{254}$) using iodine and a UV lamp for visualization. Retention factor ($R_f$) values were measured using a 5×2 cm TLC plate in a developing chamber containing the solvent system described. Melting points were measured with a Stuart Melting Point Apparatus (SMP30) in Celsius degrees and were uncorrected. $^1H$ and $^{13}C$ NMR experiments were performed on a 500 MHz instrument. Chemical shifts are reported in parts per million (ppm) downstream from the internal tetramethylsilane standard. Spin multiplicities are described as s (singlet), d (doublet), dd (double doublets), t (triplet), (td) triple doublets or m (multiplet). Coupling constants are reported in Hertz (Hz). ESI mass spectrometry was performed on a Q-TOF high-resolution mass spectrometer or Q-TOF Ultim LC-MS. Optical rotations were measured with a digital polarimeter using a 100 mm cell of 10 mL capacity.

Biology

Chemicals and Cell Culture

The tested compounds were dissolved in DMSO at a concentration of 100 mM and further diluted in PBS supplemented with 10% (v/v) DMSO. When necessary dissolution was enhanced by incubation at 50° C. and sonication at maximum output for 10 min. Hepa1.6 cell line (#CRL-1830, ATCC) was cultured in DMEM culture medium containing 1 g $L^{-1}$ glucose, 10% fetal bovine serum, 2 mM glutamine, 100 U $mL^{-1}$ Penicillin and 100 µg $mL^{-1}$ Streptomycin and 30 µM oleic acid. Cells were seeded at a density of 20000 cells per well in 96 well plates and incubated for several hours to allow the cells to attach at 37° C. with 5% $CO_2$. Cells were then supplemented with the test substances at indicated concentrations (0.01-50 µM) and incubated for indicated time periods (24-48 h).

For all assays the tested substances were further diluted in 10% DMSO/PBS and added to the cells at the indicated concentrations with a final DMSO concentration of 0.01%. Negative vehicle controls were treated with 0.01% DMSO. Positive control was treated with 10 µM oligomycin or 10 µM FCCP (Carbonyl cyanide-4-(trifluoromethoxy) phenylhydrazone).

Cytotoxicity

Cytotoxicity was assessed using the Pierce LDH Cytotoxicity Assay Kit (#88953, Thermo Fisher). After cells were culture with the test substances for 24 h 20 µL of the cell culture medium were transferred to a new 96 well plate and the cytotoxicity assay was performed as per the manufacturer's instructions. Absorbance was measure at 490 nm and background at 680 nm. The signal intensity of untreated cells was considered as the background signal of spontaneous LDH release and subtracted from all measurements. Cytotoxicity was expressed as the percentage of maximum signal intensity observed in freshly lysed cells.

Mitochondrial Membrane Potential

Mitochondrial membrane potential ($\Delta\Psi m$) was assessed using the tetramethylrhodamine (TMRE) fluorophore. The cells were incubated with the test substances for 24 h and then loaded with TMRE at a final concentration of 200 nM for 45 min at 37° C. Positive control wells were treated with 10 µM FCCP 30 min before loading the cells with TMRE. The medium was removed and the cells were washed with PBS and supplemented with fresh culture medium. Fluorescence intensity of TRME was immediately measured (ex/em: 545/580 nm) using a plate reader spectrophotometer. The results were normalized to the fluorescence intensity measured in mock treated negative controls and the positive controls treated with 10 µM FCCP.

ATP Content

Cells were treated for 24 h with the test substances at the indicated concentrations. The cellular ATP content was assessed using the CellTiter-Glo Assay (#G7571, Promega) as per the manufacturer's instructions. Luminescence was detected in a plate reader spectrophotometer. The results were normalized to the luminescence intensity measured in mock treated negative controls and the positive controls treated with 10 µM oligomycin.

Cellular Re Dox Potential

Cells were treated for 24 h with the test substances or controls (0.1% DMSO, 10 µM FCCP and 10 µM oligomycin). AlamarBlue reagent (resazurin, #BUF012A, Bio-Rad) was added to the cells in an amount equal to 10% of the culture medium per well during the last 4 h of incubations. Fluorescence was measured at ex/em: 550/590 nm. Results were normalized to the fluorescence intensity measured in blank wells and wells containing fully reduced AlamarBlue reagent. Results were expressed relative to the mock treated negative controls.

BrdU Incorporation/Cell Proliferation Assay Proliferation

Cells were incubated for a total of 48 h with the tested substances. During the last 12 h the cells were supplemented with 200 µM BrdU (#ab126556, Abcam). After the incubation period cells were washed with PBS. Following that the cells fixed and permeabilized using the reagents of the kit and labeled for 1 h with anti-BrdU antibodies conjugated with peroxidase. After washing the fixed cells 5 times with PBS the wells were incubated with peroxidase substrate TMB. The reaction was stopped after 30 min. The signal intensity was measure at absorbance 450 nm. Results were normalized to controls samples treated with vehicle (0.01% DMSO, negative control) or 10 μM oligomycin.

Lymphocyte and Splenocyte Preparation

Spleen and lymph nodes were collected from C57BL/6J mice and stored in RPMI medium on ice until further processing. Further procedures were performed using a laminar flow hood. Single cell suspensions were created by shearing the organs between two microscopy slides. Cell suspensions were passed through a 70 μm cell strainer to exclude remaining tissue chunks. Cells were washed in PBS and centrifuged at 300 g for 5 min at 4° C. During the preparation of splenic single cell suspension, erythrocytes were removed by incubating the cells for 5 min at rt in RBC lysis buffer followed by extensive washing in PBS. Cells were resuspended in RPMI medium and cell count was determined. Lymphocytes were kept on ice until further use.

T Cell Enrichment from Splenocytes

T cell was enriched from the splenocytes by negative selection using magnetic bead separation (Pan T cell isolation kit II, mouse, #130-095-130, Miltenyi) achieving more than 90% purity. The cells were kept in RPMI medium until further use.

Activation Induced Immune Cell Proliferation in T Cells and Lymphocytes

A total $17 \times 10^6$ cells were suspended in 15 mL Krebs Ringer buffer (with HEPES, 1 g $L^{-1}$ glucose, 1 mM pyruvate), supplemented with 30 μL of Cytopainter blue stock solution (500×) (#ab176726, Abcam) and incubated for 30 min at 37° C. to let the CFSE analog accumulate in the cells. The remaining Cytopainter reagent that was not incorporated into the cells was quenched by addition of 10 mL FCS and incubated for 5 min at rt. Another 25 mL of PBS were added and cells were centrifuged at 300 g for 5 min at rt. The cells were then suspended in 12.75 mL of complete RPMI culture medium. $2 \times 10^5$ cells in a volume of 150 μL were added to the wells of 96 well plates. The cytopainter-loaded cells were supplemented with the test substances, or DMSO as a negative control and oligomycin as a positive control.

Cytopainter loaded T cells were stimulated using two different approaches. Either T cells stimulated by plate bound anti-CD3 antibodies (coated at 1 μg/mL) and soluble anti-CD28 antibodies (at a final concentration of 0.2 μg $mL^{-1}$), or in separate replicates by addition of the cytokines IL-2 (50 ng $mL^{-1}$) and IL-7 (10 ng $mL^{-1}$) to stimulate T cells proliferation and survival.

Cytopainter loaded lymphocytes were stimulated with PMA (15 ng $mL^{-1}$) and Ionomycin (0.5 μg $mL^{-1}$). All cells were incubated for 60 h at 37° C., 5% $CO_2$. Lymphocytes were then washed with 2% FBS in PBS, supplemented with anti-CD16/CD32 antibodies (to block unspecific Fc-receptor binding) and incubated for 10 min at 4° C. Subsequently cells were incubated for 20 min at 4° C. with anti-CD3 antibodies conjugated to FITC (clone: 145-2C11, #11-0031-82, eBioscience) and anti-B220 antibodies conjugated to PerCP-Cy5.5 (clone:RA3-6B2, #45-0452-82, eBioscience) to label T cells and B cells, respectively. Cells were subsequently washed with 2% FBS in PBS analyzed.

Cell proliferation was then analyzed by assessing the fluorescence intensity of cytopainter in the cells by flow cytometry. Reduced intensity of cytopainter dye indicates cells that have undergone cell division. Data was analyzed using FlowJo v10.4.2. Proliferation parameters were derived using the FlowJo Proliferation Tool. The Expansion index determines the fold-expansion of the overall culture. The Division index expresses the average number of cell divisions that a cell in the original population has undergone and also includes the cells that have never divided.

Statistical analysis was performed using Graph Pad Prism v6.07. Comparison of the test substances was performed by ANOVA with Dunnett's post hoc test unless otherwise stated. Non-linear regression was fitted to the data points using Graph Pad.

Example-1

It describes the process for the preparation of compounds of general formula V and the characterization data for the selected compounds of this class.

Aldehyde (III, 0.5 mmol) was dissolved in DCM (2 mL) and a solution of amine (IV, 0.5 mmol) in DCM (2.0 mL) was added dropwise at −78° C. Then, a solution of TFA (1.0 mmol) in DCM (1 mL) was added dropwise at −78° C. and slowly warmed to room temperature and stirring was continued for 2-4 h. After completion, the reaction mixture was diluted with DCM (30 mL) and washed with saturated sodium bicarbonate solution (2×20 mL). The organic layer was separated, dried over $Na_2SO_4$ and concentrated under vacuum. The crude was purified on flash chromatography, using EtOAc/hexane as an eluent to produce the compounds of general formula V.

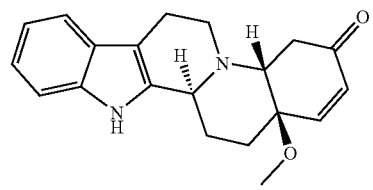

(2aR,6aR,14bS)-2a-Methoxy-2,2a,6,6a,8,9,14,14b-octahydroindolo[2',3':3,4]pyrido[1,2-a]quinolin-5(1H)-one (1a): Off-white solid, 107 mg, 67% yield; mp: 204-207° C.; $R_f$=0.45 (silica gel, hexane/EtOAc 1:1); $^1H$ NMR (500 MHz, $CDCl_3$): δ 7.79 (s, 1H), 7.48 (t, J=7.6 Hz, 1H), 7.31 (t, J=8.4 Hz, 1H), 7.19-7.09 (m, 2H), 6.86 (d, J=10.3 Hz, 1H), 6.12 (d, J=10.3 Hz, 1H), 3.96 (d, J=10.0 Hz, 1H), 3.83-3.74 (m, 1H), 3.32 (s, 3H), 3.11-3.05 (m, 1H), 3.03-2.90 (m, 2H), 2.85-2.73 (m, 3H), 2.09-1.97 (m, 2H), 1.95-1.83 (m, 2H); $^{13}C$ NMR (125 MHz, $CDCl_3$): δ 199.4, 155.5, 136.2, 134.5, 130.6, 127.3, 121.5, 119.5, 118.2, 110.7, 108.6, 74.7, 59.1, 50.7, 50.4, 49.3, 35.3, 30.3, 24.9, 22.1; HRMS (m/z): $[M+H]^+$ calcd. for $C_{20}H_{23}N_2O_2$, 323.1759; found 323.1764.

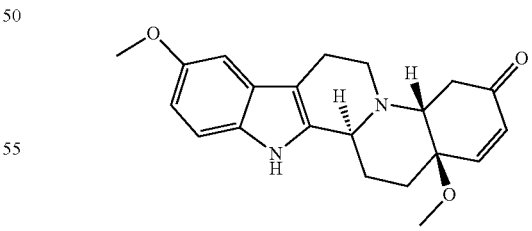

(2aR,6aR,14bS)-2a,11-Dimethoxy-2,2a,6,6a,8,9,14,14b-octahydroindolo[2',3':3,4]pyrido[1,2-a]quinolin-5(1H)-one (1b): Off-white solid, 121 mg, 69% yield; mp: 216-218° C.; $R_f$=0.4 (silica gel, hexane/EtOAc 1:1); $^1H$ NMR (500 MHz, $CDCl_3$): δ 7.67 (s, 1H), 7.21 (d, J=8.7 Hz, 1H), 6.94 (d, J=2.0 Hz, 1H), 6.88-6.79 (m, 2H), 6.11 (d, J=10.3 Hz, 1H), 3.92 (d, J=10.7 Hz, 1H), 3.87 (s, 3H), 3.77 (t, J=8.6 Hz, 1H), 3.33 (s, 3H), 3.11-3.04 (m, 1H), 3.02-2.86 (m, 2H), 2.80 (d, J=8.6 Hz, 2H), 2.72 (d, J=14.3 Hz, 1H), 2.10-1.96 (m, 2H), 1.93-1.80 (m, 2H); $^{13}$C NMR (125 MHz, CDCl$_3$): δ 199.3, 155.5, 154.1, 135.4, 131.2, 130.6, 127.7, 111.4, 111.2, 108.5, 100.5, 74.7, 59.1, 55.9, 50.7, 50.5, 49.3, 35.3, 30.4, 24.9, 22.2; HRMS (m/z): [M+H]$^+$ calcd. for C$_{21}$H$_{25}$N$_2$O$_3$, 353.1865, found 353.1871.

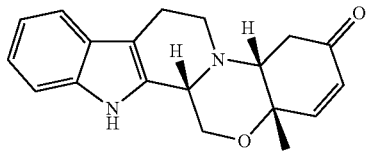

(2aS,6aR,14bS)-2a-methyl-6,6a,8,9,14,14b-hexahydro-1H-benzo[5',6'][1,4]oxazino[4',3':1,2]pyrido[3,4-b]indol-5(2aH)-one (1c): White solid, 32 mg, 21% yield; mp: 226-228° C.; R$_f$=0.5 (silica gel, hexane/EtOAc 1:1); $^1$H NMR (500 MHz, CDCl$_3$): δ 7.66 (s, 1H), 7.48 (d, J=7.8 Hz, 1H), 7.31 (d, J=8.0 Hz, 1H), 7.19-7.13 (m, 1H), 7.11 (dd, J=11.0, 3.9 Hz, 1H), 6.64 (dd, J=10.1, 2.1 Hz, 1H), 6.06 (d, J=10.1 Hz, 1H), 4.09 (d, J=7.9 Hz, 1H), 3.81-3.71 (m, 2H), 3.54 (dd, J=11.3, 4.5 Hz, 1H), 3.11-3.02 (m, 2H), 2.89-2.79 (m, 1H), 2.79-2.67 (m, 2H), 2.34 (td, J=11.3, 3.9 Hz, 1H), 1.58 (s, 3H); $^{13}$C NMR (125 MHz, CDCl$_3$): δ 196.7, 153.2, 136.2, 130.4, 130.2, 127.0, 121.9, 119.7, 118.3, 110.8, 110.1, 74.7, 66.3, 66.1, 58.4, 46.1, 40.1, 25.6, 22.0; HRMS (m/z): [M+H]$^+$ calcd. for C$_{19}$H$_{21}$N$_2$O$_2$, 309.1603, found 309.1611.

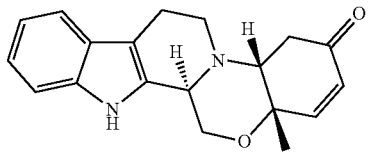

(2aS,6aR,14bR)-2a-Methyl-6,6a,8,9,14,14b-hexahydro-1H-benzo[5',6'][1,4]oxazino[4',3':1,2]pyrido[3,4-b]indol-5(2aH)-one (1d): White solid, 80 mg, 52% yield; mp: 217-219° C.; R$_f$=0.45 (silica gel, hexane/EtOAc 1:1); $^1$H NMR (500 MHz, CDCl$_3$): δ 7.95 (s, 1H), 7.52 (d, J=7.7 Hz, 1H), 7.36 (d, J=8.0 Hz, 1H), 7.23-7.17 (m, 1H), 7.17-7.12 (m, 1H), 6.70 (d, J=10.6 Hz, 1H), 6.13 (d, J=10.6 Hz, 1H), 4.27-4.14 (m, 2H), 4.10-4.01 (m, 1H), 3.32 (d, J=4.4 Hz, 2H), 3.09-2.93 (m, 3H), 2.72 (d, J=14.9 Hz, 1H), 2.64 (dd, J=16.0, 3.5 Hz, 1H), 1.51 (s, 3H); $^{13}$C NMR (125 MHz, CDCl$_3$): δ $^{13}$C NMR (125 MHz, CDCl$_3$) δ 198.9, 151.4, 136.1, 130.8, 129.9, 127.3, 121.9, 119.7, 118.1, 111.0, 109.7, 72.2, 63.5, 59.0, 52.1, 48.0, 46.1, 23.6, 19.3; HRMS (m/z): [M+H]$^+$ calcd. for C$_{19}$H$_{21}$N$_2$O$_2$, 309.1603, found 309.1607.

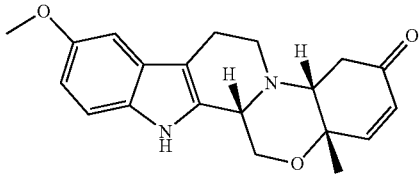

(2aS,6aR,14bS)-11-Methoxy-2a-methyl-6,6a,8,9,14,14b-hexahydro-1H-benzo[5',6'][1,4]oxazino[4',3':1,2]pyrido[3,4-b]indol-5(2aH)-one (1e): Off-white solid, 34 mg, 20% yield; mp: 243-246° C.; R$_f$=0.4 (silica gel, hexane/EtOAc 1:1); $^1$H NMR (500 MHz, CDCl$_3$): δ 7.54 (s, 1H), 7.20 (d, J=8.7 Hz, 1H), 6.92 (d, J=1.9 Hz, 1H), 6.81 (dd, J=8.7, 2.4 Hz, 1H), 6.64 (d, J=9.8 Hz, 1H), 6.05 (d, J=10.3 Hz, 1H), 4.07 (d, J=6.9 Hz, 1H), 3.85 (s, 3H), 3.75 (d, J=5.9 Hz, 2H), 3.53 (dd, J=11.2, 5.2 Hz, 1H), 3.05 (d, J=13.5 Hz, 2H), 2.86-2.74 (m, 3H), 2.38-2.30 (m, 1H), 1.57 (s, 3H); $^{13}$C NMR (125 MHz, CDCl$_3$): δ 196.7, 154.2, 153.2, 131.3, 130.4, 130.3, 127.5, 111.8, 111.5, 110.0, 100.4, 74.7, 66.3, 66.0, 58.5, 55.9, 46.2, 40.1, 25.6, 22.0; HRMS (m/z): [M+H]$^+$ calcd. for C$_{20}$H$_{23}$N$_2$O$_3$, 339.1708, found 339.1715.

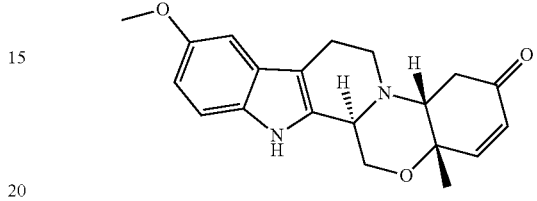

(2aS,6aR,14bR)-11-methoxy-2a-methyl-6,6a,8,9,14,14b-hexahydro-1H-benzo[5',6'][1,4]oxazino[4',3':1,2]pyrido[3,4-b]indol-5(2aH)-one (1f): Off-white solid, 89 mg, 53% yield; mp: 230-232° C.; R$_f$=0.4 (silica gel, hexane/EtOAc 1:1); $^1$H NMR (500 MHz, CDCl$_3$): δ 7.73 (s, 1H), 7.24 (d, J=8.7 Hz, 1H), 6.97 (d, J=1.7 Hz, 1H), 6.85 (dd, J=8.7, 2.1 Hz, 1H), 6.70 (d, J=10.2 Hz, 1H), 6.12 (d, J=10.2 Hz, 1H), 4.22-4.09 (m, 2H), 4.00 (dd, J=11.4, 6.0 Hz, 1H), 3.88 (s, 3H), 3.29 (d, J=4.8 Hz, 2H), 3.09-2.90 (m, 3H), 2.70-2.59 (m, 2H), 1.52 (s, 3H); $^{13}$C NMR (125 MHz, CD$_3$OD): δ 199.9, 153.6, 152.6, 131.9, 131.7, 129.3, 127.3, 111.6, 110.8, 107.9, 99.9, 72.0, 63.1, 58.8, 55.5, 53.3, 52.4, 35.6, 23.1, 18.9; HRMS (m/z): [M+H]$^+$ calcd. for C$_{20}$H$_{23}$N$_2$O$_3$, 339.1708, found 339.1719.

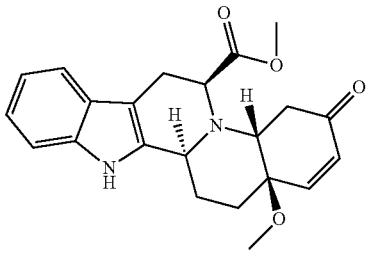

Methyl (2aR,6aR,8S,14bS)-2a-methoxy-5-oxo-1,2,2a,5,6,6a,8,9,14,14b-decahydroindolo[2',3':3,4]pyrido[1,2-a]quinoline-8-carboxylate (1g): Pinkish solid, 120 mg, 63% yield; mp: 159-161° C.; R$_f$=0.4 (silica gel, hexane/EtOAc 1:2); [α]$_D$=−275.0 (0.0047 M in acetone); $^1$H NMR (500 MHz, CDCl$_3$): δ 7.86 (s, 1H), 7.44 (d, J=7.7 Hz, 1H), 7.33 (d, J=8.0 Hz, 1H), 7.21-7.08 (m, 2H), 6.85 (d, J=10.3 Hz, 1H), 6.10 (d, J=10.3 Hz, 1H), 4.01 (d, J=11.3 Hz, 1H), 3.93 (dd, J=10.6, 7.2 Hz, 1H), 3.83 (s, 3H), 3.75 (dd, J=10.6, 3.9 Hz, 1H), 3.37 (s, 3H), 3.19-3.12 (m, 1H), 3.05-2.99 (m, 1H), 2.85-2.75 (m, 2H), 2.17-1.98 (m, 3H), 1.92-1.81 (m, 1H); $^{13}$C NMR (125 MHz, CDCl$_3$): δ 198.6, 173.1, 156.6, 136.3, 133.2, 130.9, 126.9, 122.0, 119.9, 118.2, 110.9, 106.4, 74.8, 60.9, 54.8, 52.4, 51.0, 50.4, 34.0, 30.7, 27.1, 25.9; HRMS (m/z): [M+H]$^+$ calcd. for C$_{22}$H$_{25}$N$_2$O$_4$, 381.1814, found 381.1815.

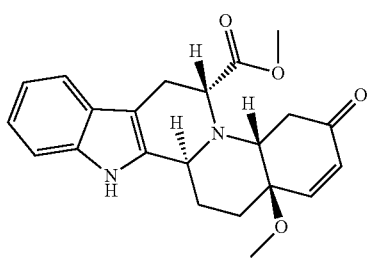

Methyl (2 aR,6aR,8R,14bS)-2a-methoxy-5-oxo-1,2,2a, 5,6,6a, 8,9,14,14b-decahydroindolo[2'3':3,4]pyrido[1,2-c]quinoline-8-carboxylate (1h): Off-white solid, 104 mg, 55% yield; mp: 158-160° C.; $R_f$=0.4 (silica gel, hexane/EtOAc 1:2); $[\alpha]_D$=+280.7 (0.0034 M in acetone); $^1$H NMR (500 MHz, CDCl$_3$): δ 8.09 (s, 1H), 7.43 (d, J=7.8 Hz, 1H), 7.36 (d, J=8.0 Hz, 1H), 7.16 (t, J=7.3 Hz, 1H), 7.10 (t, J=7.4 Hz, 1H), 6.83 (d, J=10.3 Hz, 1H), 6.08 (d, J=10.3 Hz, 1H), 3.92 (dd, J=10.8, 6.2 Hz, 2H), 3.83 (s, 3H), 3.72 (dd, J=10.6, 3.8 Hz, 1H), 3.35 (s, 3H), 3.19-3.11 (m, 1H), 3.02 (dd, J=14.8, 2.6 Hz, 1H), 2.79-2.68 (m, 2H), 2.11-1.93 (m, 3H), 1.85-1.71 (m, 2H); $^{13}$C NMR (125 MHz, CDCl$_3$): δ 198.6, 173.0, 156.6, 136.3, 133.3, 130.8, 126.9, 121.9, 119.8, 118.2, 111.0, 106.2, 74.8, 60.9, 54.8, 52.4, 51.0, 50.4, 34.0, 30.6, 27.1, 25.9; HRMS (m/z): [M+H]$^+$ calcd. for C$_{22}$H$_{25}$N$_2$O$_4$, 381.1814, found 381.1823.

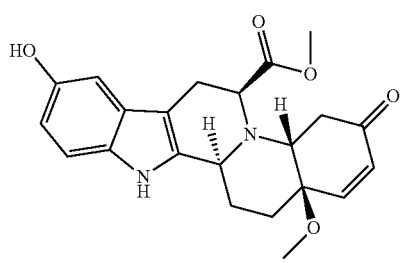

Methyl (2 aR,6aR,8S, 14bS)-11-hydroxy-2a-methoxy-5-oxo-1,2,2a, 5,6,6a, 8,9,14,14b-decahydroindolo[2'3':3,4]pyrido[1,2-c)]quinoline-8-carboxylate (1i): Brownish solid, 79 mg, 40% yield; mp: 165-167° C.; $R_f$=0.35 (silica gel, hexane/EtOAc 1:2); $[\alpha]_D$=-214.2 (0.0017 Min acetone); $^1$H NMR (500 MHz, CD$_3$OD): δ 7.13 (d, J=8.6 Hz, 1H), 6.90 (dd, J=10.4, 3.6 Hz, 1H), 6.76 (d, J=2.3 Hz, 1H), 6.64 (dd, J=8.6, 2.3 Hz, 1H), 6.05 (d, J=10.3 Hz, 1H), 3.95-3.86 (m, 1H), 3.87-3.79 (m, 4H), 3.69 (dd, J=10.5, 3.9 Hz, 1H), 3.31 (s, 3H), 3.04-2.95 (m, 1H), 2.95-2.82 (m, 2H), 2.72-2.63 (m, 1H), 2.13 (d, J=6.7 Hz, 1H), 1.99-1.84 (m, 3H); $^{13}$C NMR (125 MHz, CD$_3$OD): δ 199.5, 173.2, 156.5, 150.0, 134.4, 131.6, 129.8, 127.1, 110.9, 110.4, 103.7, 101.7, 74.9, 61.1, 55.2, 51.3, 50.4, 49.7, 33.5, 29.8, 26.4, 25.0; HRMS (m/z): [M+H]$^+$ calcd. for C$_{22}$H$_{25}$N$_2$O$_5$, 397.1763, found 397.1774.

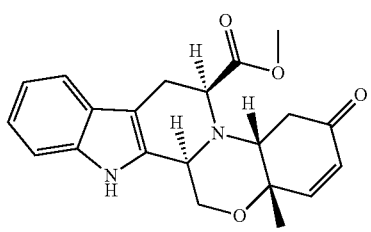

Methyl (2 aS,6aR,8S,14bR)-2a-methyl-5-oxo-2a,5,6,6a, 8,9,14,14b-octahydro-1H-benzo[5',6'][1,4]oxazino[4',3':1, 2]pyrido[3,4-b]indole-8-carboxylate (1j): Off-white solid, 78 mg, 43% yield; mp: 150-153° C.; $R_f$=0.45 (silica gel, hexane/EtOAc 1:1); $[\alpha]_D$=-252.4 (0.0054 M in acetone); $^1$H NMR (500 MHz, CDCl$_3$): δ 7.89 (s, 1H), 7.51 (d, J=7.7 Hz, 1H), 7.36 (d, J=8.0 Hz, 1H), 7.25-7.19 (m, 1H), 7.16 (dd, J=11.0, 3.9 Hz, 1H), 6.73 (d, J=10.2 Hz, 1H), 6.08 (d, J=10.2 Hz, 1H), 4.36-4.29 (m, 1H), 4.17 (dd, J=11.2, 2.8 Hz, 1H), 3.99 (dd, J=11.2, 9.1 Hz, 1H), 3.86-3.76 (m, 4H), 3.46-3.38 (m, 1H), 3.22-3.12 (m, 1H), 3.11-2.94 (m, 2H), 2.58 (dd, J=15.9, 3.7 Hz, 1H), 1.60 (d, J=10.6 Hz, 3H); $^{13}$C NMR (125 MHz, CDCl$_3$): δ198.6, 172.8, 151.0, 136.4, 129.6, 126.8, 122.7, 120.1, 118.3, 111.2, 108.1, 76.9, 71.6, 64.0, 60.7, 56.9, 52.5, 52.0, 33.9, 25.0, 22.9; HRMS (m/z): [M+H]$^+$ calcd. for C$_{21}$H$_{23}$N$_2$O$_4$, 367.1657, found 367.1660.

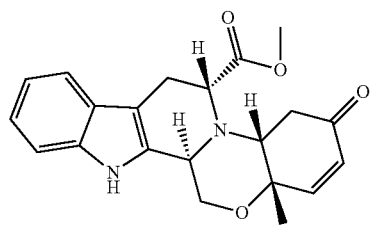

Methyl (2 aS,6aR,8R,14bR)-2a-methyl-5-oxo-2a,5,6,6a, 8,9,14,14b-octahydro-1H-benzo[5',6'][1,4]oxazino[4 ',3':1, 2]pyrido[3,4-b]indole-8-carboxylate (1k): Off-white solid, 95 mg, 52% yield; mp: 150-152° C.; $R_f$=0.45 (silica gel, hexane/EtOAc 1:1); $[\alpha]_D$=+250.0 (0.0027 M in acetone); $^1$H NMR (500 MHz, Acetone-d$_6$): δ 10.06 (s, 1H), 7.46 (d, J=7.8 Hz, 1H), 7.32 (d, J=8.0 Hz, 1H), 7.11-7.05 (m, 1H), 7.05-6.99 (m, 1H), 6.72 (d, J=10.2 Hz, 1H), 5.93 (d, J=10.2 Hz, 1H), 4.36 (d, J=9.2 Hz, 1H), 4.27 (dd, J=11.2, 3.5 Hz, 1H), 3.89 (t, J=9.7 Hz, 1H), 3.83-3.74 (m, 4H), 3.35 (dd, J=11.4, 3.8 Hz, 1H), 3.13-2.93 (m, 2H), 2.81 (t, J=10.1 Hz, 1H), 2.53 (dd, J=15.5, 3.8 Hz, 1H), 1.59 (s, 3H); $^{13}$C NMR (125 MHz, Acetone-d$_6$): δ 198.7, 173.3, 151.4, 137.7, 137.6, 131.3, 129.6, 127.7, 122.2, 119.9, 118.6, 111.9, 107.3, 71.7, 64.4, 61.5, 57.8, 52.4, 33.7, 30.3, 22.7; HRMS (m/z): [M+H]$^+$ calcd. for C$_{21}$H$_{23}$N$_2$O$_4$, 367.1657, found 367.1649.

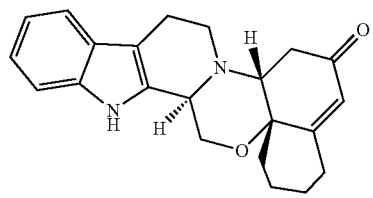 [SMILES: O=C1C=C2CCCC[C@]23OC[C@H]2c4[nH]c5ccccc5c4CCN2[C@@H]3C1]

(2aS,9aR, 17bR)-3,4,5,6,9,9a, 11,12,17,17b-Decahydro-1H,8H-naphtho[1'',8a'':5',6'][1,4]oxazino[4',3': 1,2]pyrido[3,4-b]indol-8-one (1l): White solid, 88 mg, 55% yield; mp: 232-235° C.; $R_f$=0.45 (silica gel, hexane/EtOAc 1:1); $^1$H NMR (500 MHz, CDCl$_3$): δ 7.83 (s, 1H), 7.52 (d, J=7.8 Hz, 1H), 7.34 (d, J=7.8 Hz, 1H), 7.22-7.09 (m, 2H), 5.91 (s, 1H), 4.16 (d, J=8.4 Hz, 1H), 4.05 (dd, J=10.6, 2.8 Hz, 1H), 3.84 (t, J=10.6 Hz, 1H), 3.21-3.12 (m, 2H), 3.12-3.02 (m, 1H), 3.11-2.92 (m, 3H), 2.80-2.70 (m, 1H), 2.68-2.51 (m, 2H), 2.36 (d, J=13.9 Hz, 1H), 1.94 (d, J=12.2 Hz, 1H), 1.73-1.57 (m, 2H), 1.53-1.39 (m, 1H), 1.21 (t, J=12.9 Hz, 1H); $^{13}$C NMR (125 MHz, CDCl$_3$): δ 199.6, 162.5, 136.3, 130.7, 127.1, 125.2, 121.9, 119.7, 118.2, 110.9, 109.8, 72.5, 63.2, 60.6, 50.6, 48.9, 32.6, 32.2, 32.1, 26.9, 21.4, 20.2; HRMS (m/z): [M+H]$^+$ calcd. for $C_{22}H_{25}N_2O_2$, 349.1916, found 349.1910.

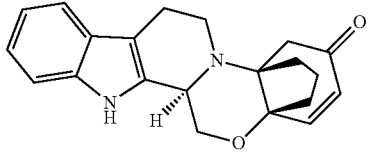 [SMILES: O=C1C=C[C@@]23CCC[C@]2(C1)N1CCc2c([nH]c4ccccc24)[C@@H]1CO3]

(2aS,6aR,14bR)-8,9,14,14b-Tetrahydro-1H-2a,6a-propanobenzo[5',6'][1,4]oxazino[4',3':1,2]pyrido[3,4-b]indol-5(6H)-one (1m): Off-white solid, 50 mg, 30% yield; mp: 126-228° C.; $R_f$=0.5 (silica gel, hexane/EtOAc 1:1); $^1$H NMR (500 MHz, CDCl$_3$): δ 7.84 (s, 1H), 7.52 (d, J=7.5 Hz, 1H), 7.34 (d, J=7.5 Hz, 1H), 7.16 (dt, J=26.8, 7.2 Hz, 2H), 6.62 (t, J=12.2 Hz, 1H), 6.08 (d, J=10.1 Hz, 1H), 4.17-4.06 (m, 2H), 3.93 (t, J=10.6 Hz, 1H), 3.32 (d, J=7.3 Hz, 1H), 3.03 (d, J=15.6 Hz, 1H), 2.91-2.80 (m, 2H), 2.61-2.45 (d, J=14.3 Hz, 1H), 2.62-2.43 (m, 2H), 2.22 (t, J=9.7 Hz, 1H), 1.98-1.87 (m, 1H), 1.64-1.44 (m, 3H); $^{13}$C NMR (125 MHz, CDCl$_3$) δ: 200.1, 150.4, 136.3, 130.9, 128.9, 127.0, 121.9, 119.7, 118.2, 110.9, 110.4, 80.3, 63.5, 62.5, 51.8, 43.1, 35.8, 33.8, 30.4, 22.6, 19.0; HRMS (m/z): [M+H]$^+$ calcd. for $C_{21}H_{23}N_2O_2$, 335.1759, found 335.1754.

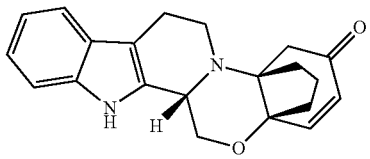 [SMILES: O=C1C=C[C@@]23CCC[C@]2(C1)N1CCc2c([nH]c4ccccc24)[C@H]1CO3]

(2 aS,6aR,14bR)-8,9,14,14b-Tetrahydro-1H-2a,6a-propanobenzo[5',6'][1,4]oxazino[4',3':1,2]pyrido[3,4-b]indol-5(6H)-one (1n): Off-white solid, 50 mg, 30% yield; mp: 200-202° C.; $R_f$=0.55 (silica gel, hexane/EtOAc 1:1); $^1$H NMR (500 MHz, CDCl$_3$): δ 7.72 (s, 1H), 7.53-7.41 (m, 1H), 7.36-7.25 (m, 1H), 7.19-7.06 (m, 2H), 6.67 (d, J=10.2 Hz, 1H), 6.08 (d, J=10.2 Hz, 1H), 4.15 (d, J=9.7 Hz, 1H), 4.06 (dd, J=10.8, 3.0 Hz, 1H), 3.69 (t, J=10.8 Hz, 1H), 3.47 (dd, J=11.3, 4.8 Hz, 1H), 2.94 (d, J=16.0 Hz, 1H), 2.85-2.74 (m, 1H), 2.67 (d, J=14.9 Hz, 1H), 2.60-2.47 (m, 2H), 2.41 (td, J=11.5, 3.4 Hz, 1H), 2.24-1.99 (m, 3H), 1.97-1.85 (m, 1H), 1.48-1.35 (m, 1H); $^{13}$C NMR (125 MHz, CDCl$_3$): δ 197.8, 150.5, 136.2, 130.9, 130.8, 127.1, 121.7, 119.7, 118.2, 110.8, 110.2, 83.2, 71.5, 65.7, 51.9, 45.8, 43.5, 36.6, 25.7, 22.6, 20.5; HRMS (m/z): [M+H]$^+$ calcd. for $C_{21}H_{23}N_2O_2$, 335.1759, found 335.1755.

Example 2

It describes the process for the preparation of compounds of general formula I and the characterization data for the selected compounds of this class.

Compound of general formula (V, 0.2 mmol) was dissolved in methanol (1.0 mL) and 10 wt % Pd/C (5 mol %) was added and stirring was continued under hydrogen atmosphere for 3-4 h at rt. After completion, the reaction mixture was filtered through a celite pad and the filtrate was concentrated. The crude was purified on flash chromatography, using EtOAc in hexane as an eluent to produce compounds of general formula I.

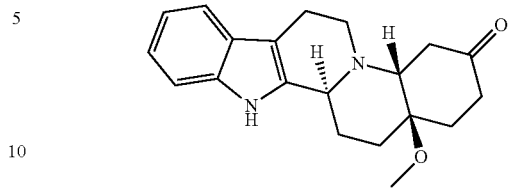

(2aR,6aR,14bS)-2a-Methoxy-2,2a, 3,4,6,6a,8,9,14,14b-decahydroindolo[2',3': 3,4]pyrido[1,2-a]quinolin-5(1H)-one (1o): Off-white solid, 58 mg, 90% yield; mp: 183-185° C.; $R_f$=0.45 (silica gel, hexane/EtOAc 1:1); $^1$H NMR (500 MHz, CDCl$_3$): δ 7.86 (s, 1H), 7.48 (d, J=7.6 Hz, 1H), 7.35 (d, J=7.6 Hz, 1H), 7.20-7.09 (m, 2H), 4.29-4.21 (m, 1H), 3.48-3.36 (m, 1H), 3.28-3.21 (m, 4H), 3.05-2.96 (m, 1H), 2.87 (t, J=13.0 Hz, 2H), 2.62 (d, J=13.0 Hz, 2H), 2.53-2.37 (m, 2H), 2.36-2.27 (m, 1H), 2.15-2.05 (m, 2H), 2.03-1.88 (m, 2H), 1.70-1.59 (s, 1H); $^{13}$C NMR (125 MHz, CDCl$_3$): δ 211.1, 135.9, 133.2, 127.8, 121.6, 119.7, 118.2, 110.9, 109.0, 73.6, 61.0, 53.5, 48.6, 48.2, 38.3, 37.2, 28.5, 27.3, 24.6, 18.8; HRMS (m/z): [M+H]$^+$ calcd. for $C_{20}H_{25}N_2O_2$, 325.1916, found 325.1908.

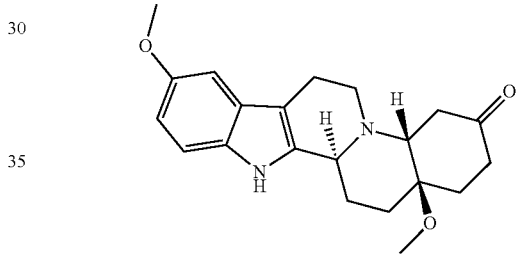

(2aR,6aR,14bS)-2a,11-dimethoxy-2,2a,3,4,6,6a,8,9,14,14b-decahydroindolo[2',3':3,4]pyrido[1,2-a]quinolin-5(1H)-one (1p): Off-white solid, 67 mg, 95% yield; mp: 180-183° C.; $R_f$=0.4 (silica gel, hexane/EtOAc 1:1); $^1$H NMR (500 MHz, Acetone): δ 9.73 (s, 1H), 7.17 (t, J=10.1 Hz, 1H), 6.91 (d, J=2.4 Hz, 1H), 6.68 (dd, J=8.7, 2.4 Hz, 1H), 4.21-4.12 (m, 1H), 3.78 (s, 3H), 3.30 (dd, J=12.8, 4.6 Hz, 1H), 3.24-3.17 (m, 4H), 2.95-2.88 (m, 1H), 2.85-2.69 (m, 3H), 2.64 (dd, J=13.8, 7.0 Hz, 1H), 2.55-2.49 (m, 1H), 2.38-2.30 (m, 1H), 2.25 (dt, J=16.0, 5.3 Hz, 2H), 2.18-2.12 (m, 1H), 2.11-2.07 (m, 1H), 1.91 (dd, J=12.3, 6.3 Hz, 1H), 1.59-1.50 (m, 1H); $^{13}$C NMR (125 MHz, Acetone): δ 209.6, 154.8, 136.1, 132.3, 128.9, 112.3, 111.3, 108.3, 100.7, 74.3, 61.8, 55.8, 54.0, 48.9, 48.4, 38.6, 37.7, 29.2, 28.2, 25.1, 20.1; HRMS (m/z): [M+H]$^+$ calcd. for $C_{21}H_{27}N_2O_3$, 355.2021, found 355.2029.

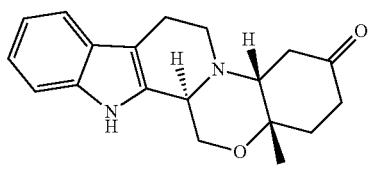

(2aS,6aR,14bR)-2a-Methyl-3,4,6,6a,8,9,14,14b-octahydro-1H-benzo[5',6'][1,4]oxazino[4',3':1,2]pyrido[3,4-k]

indol-5(2aH)-one (1q): Off-white solid, 57 mg, 92% yield; mp: 236-238° C.; $R_f$=0.5 (silica gel, hexane/EtOAc 1:1); $^1$H NMR (500 MHz, CDCl$_3$): δ 7.74 (s, 1H), 7.49 (d, J=7.7 Hz, 1H), 7.32 (d, J=7.9 Hz, 1H), 7.16 (t, J=7.4 Hz, 1H), 7.11 (t, J=7.3 Hz, 1H), 4.17-4.05 (m, 2H), 3.89 (t, J=10.6 Hz, 1H), 3.13-3.02 (m, 2H), 3.01-2.91 (m, 1H), 2.90-2.81 (m, 2H), 2.81-2.67 (m, 2H), 2.44 (d, J=9.2 Hz, 1H), 2.19 (d, J=11.9 Hz, 2H), 1.80-1.71 (m, 1H), 1.49 (s, 3H); $^{13}$C NMR (125 MHz, CDCl$_3$): δ 211.7, 136.4, 131.0, 127.1, 121.9, 119.8, 118.3, 111.0, 109.7, 72.2, 64.6, 64.5, 49.8, 49.3, 36.7, 36.6, 35.8, 22.7, 22.1. HRMS (m/z): [M+H]$^+$ calcd. for $C_{19}H_{23}N_2O_2$, 311.1759, found 311.1755.

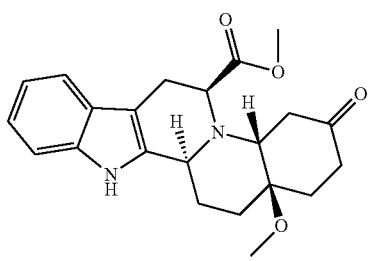

Methyl (2aR,6aR,8S,14bS)-2a-methoxy-5-oxo-1,2,2a,3,4,5,6,6a,8,9,14,14b-dodecahydroindolo[2',3':3,4]pyrido[1,2-a]quinoline-8-carboxylate (1r): Off-white solid, 64 mg, 85% yield; mp: 114-116° C.; $R_f$=0.4 (silica gel, hexane/EtOAc 1:2); $[α]_D$=−92.8 (0.0018 M in acetone); $^1$H NMR (500 MHz, Acetone) δ: 10.03 (s, 1H), 7.42 (d, J=7.7 Hz, 1H), 7.32 (t, J=10.0 Hz, 1H), 7.07 (t, J=6.0 Hz, 1H), 7.00 (t, J=6.0 Hz, 1H), 4.16-4.08 (m, 1H), 3.78 (s, 3H), 3.69 (dd, J=10.8, 3.8 Hz, 1H), 3.47 (dd, J=10.8, 5.0 Hz, 1H), 3.25 (s, 3H), 3.08-2.98 (m, 1H), 2.96-2.78 (m, 2H), 2.58-2.43 (m, 2H), 2.37-2.28 (m, 1H), 2.27-2.16 (m, 2H), 2.17-2.09 (m, 1H), 2.04-1.95 (m, 1H), 1.90-1.81 (m, 1H), 1.68-1.59 (m, 1H); $^{13}$C NMR (125 MHz, Acetone): δ 208.6, 173.6, 137.6, 137.4, 135.4, 127.8, 121.7, 119.7, 118.4, 111.8, 106.2, 73.9, 62.7, 58.7, 52.2, 48.2, 38.1, 37.1, 30.6, 28.5, 26.6, 26.5; HRMS (m/z): [M+H]$^+$ calcd. for $C_{22}H_{27}N_2O_4$, 383.1970, found 383.1981.

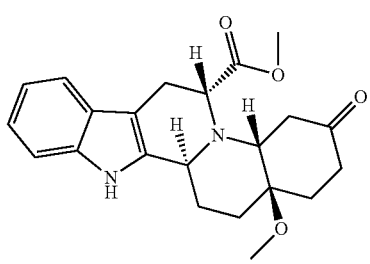

Methyl (2 aR, 6aR, 8R, 14b S)-2a-methoxy-5-oxo-1,2,2a,3,4,5,6,6a, 8,9,14,14b-dodecahydroindolo[2',3':3,4]pyrido[1,2-a]quinoline-8-carboxylate (1s): Off-white solid, 66 mg, 87% yield; mp: 113-16° C.; $R_f$=0.4 (silica gel, hexane/EtOAc 1:2); $[α]_D$=+95.2 (0.0005 M in acetone); NMR (500 MHz, Acetone): δ 9.99 (s, 1H), 7.43 (d, J=7.7 Hz, 1H), 7.32 (d, J=8.0 Hz, 1H), 7.06 (t, J=7.5 Hz, 1H), 7.00 (t, J=7.1 Hz, 1H), 4.17-4.07 (m, 1H), 3.79 (s, 3H), 3.69 (dd, J=10.6, 3.2 Hz, 1H), 3.47 (dd, J=10.6, 4.8 Hz, 1H), 3.25 (s, 3H), 3.07-2.99 (m, 1H), 2.94-2.88 (m, 1H), 2.85-2.80 (m, 1H), 2.59-2.43 (m, 2H), 2.38-2.27 (m, 1H), 2.27-2.18 (m, 2H), 2.17-2.09 (m, 1H), 2.05-1.96 (m, 1H), 1.90-1.80 (m, 1H), 1.68-1.60 (m, 1H); $^{13}$C NMR (125 MHz, Acetone): δ 208.6, 173.6, 137.6, 135.4, 127.8, 121.7, 119.7, 118.4, 111.8, 106.2, 73.9, 62.7, 58.7, 52.3, 52.2, 48.2, 38.1, 37.1, 30.6, 28.5, 26.6, 26.5; HRMS (m/z): [M+H]$^+$ calcd. for $C_{22}H_{27}N_2O_4$, 383.1970, found 383.1964.

Example 3

It describes the process for the preparation of compounds of general formula II, and the characterization data for the selected compounds of this class.

Compound of general formula I (0.1 mmol) was dissolved in THF:AcOH:water (0.4:0.4:0.4 mL) and NBS (0.1 mmol) was added slowly at −10° C. The reaction mixture was slowly warmed to room temperature and stirring continued for 2 h. After completion, the reaction mixture was quenched slowly with saturated sodiumbicarbonate solution at 0° C. Then, the reaction mixture was diluted with DCM (30 mL) and washed with water (2×20 mL). The organic layer was separated, dried over Na$_2$SO$_4$ and concentrated under vacuum. The crude was purified on flash chromatography, using EtOAc in hexane as an eluent to obtain the title compounds of general formula II.

(3 S,3a'S,5a'R,9a'R)-5a'-methoxy-1',2',3a',4',5',5a',6',7',9',9a'-decahydro-8'H-spiro[indoline-3,3'-pyrrolo[1,2-c]quinoline]-2,8'-dione (1t): Off-white solid, 47% yield; $^1$H NMR (500 MHz, CDCl$_3$) δ 8.74 (s, 1H), 7.24-7.15 (m, 2H), 7.08-6.98 (m, 1H), 6.90 (d, J=7.3 Hz, 1H), 3.49-3.40 (m, 1H), 3.30 (s, 3H), 3.04-2.93 (m, 1H), 2.69-2.58 (m, 1H), 2.54-2.28 (m, 6H), 2.23 (d, J=12.9 Hz, 1H), 2.02-1.89 (m, 2H), 1.82 (d, J=8.1 Hz, 1H), 1.68-1.57 (m, 1H), 1.46-1.35 (m, 1H). 1.35-1.29 (m, 1H); $^{13}$C NMR (125 MHz, CDCl$_3$) δ 211.0, 181.3, 141.0, 134.0, 128.1, 123.1, 122.7, 109.7, 75.3, 73.7, 69.2, 56.1, 51.5, 49.0, 40.8, 36.6, 34.9, 31.9, 27.0, 22.2; LCMS (ESI): m/z 341 [M+H]$^+$.

Methyl (1'S,3 S,3a'S,5a'R,9a'R)-5a'-methoxy-2,8'-dioxo-1',2',3a',4',5a',6',7',8',9',9a'-decahydro-5H-spiro[indoline-3,3'-pyrrolo[1,2-d]quinoline]-1'-carboxylate (1u): Off-white solid, 40% yield; NMR (500 MHz, CDCl$_3$) δ 7.77 (s, 1H), 7.37 (d, J=7.4 Hz, 1H), 7.22-7.17 (m, 1H), 7.07-7.01 (m, 1H), 6.84 (d, J=7.7 Hz, 1H), 4.21 (d, J=8.4 Hz, 1H), 3.57 (dd, J=11.4, 3.0 Hz, 1H), 3.32 (s, 3H), 3.18-3.14 (m, 1H), 2.97 (dd, J=14.8, 4.2 Hz, 1H), 2.77 (dd, J=13.9, 9.2 Hz, 1H), 2.68-2.59 (m, 1H), 2.52-2.43 (m, 1H), 2.39-2.33 (m, 1H), 2.28-2.20 (m, 1H), 2.14-2.07 (m, 1H), 1.96-1.90 (m, 1H), 1.82 (dd, J=13.9, 6.1 Hz, 1H), 1.59-1.51 (m, 1H), 1.49-1.41 (m, 1H), 1.33-1.27 (m, 1H); $^{13}$C NMR (125 MHz, CDCl$_3$) δ 211.1, 180.6, 174.3, 140.6, 133.0, 128.3, 124.3, 123.1, 109.3, 73.8, 69.9, 64.0, 60.4, 56.1, 51.6, 49.1, 40.4, 39.4, 36.5, 31.3, 26.7, 22.4; LCMS (ESI): m/z 399 [M+H]$^+$.

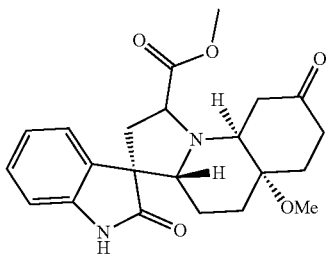

Methyl (1'R,3 S,3 8',9',9a'-decahydro-5H-spiro[indoline-3,3'-pyrrolo[1,2-d]quinoline]-1'-carboxylate (1v): Off-white solid, 42% yield; NMR (500 MHz, CDCl$_3$) δ 7.79 (s, 1H), 7.40 (d, J=7.4 Hz, 1H), 7.22 (dd, J=7.6, 6.9 Hz, 1H), 7.07 (t, J=7.4 Hz, 1H), 6.86 (d, J=7.7 Hz, 1H), 4.23 (d, J=8.2 Hz, 1H), 3.78 (s, 3H), 3.59 (dd, J=11.4, 3.3 Hz, 1H), 3.34 (s, 3H), 3.20-3.16 (m, 1H), 3.00 (dd, J=14.8, 4.2 Hz, 1H), 2.79 (dd, J=13.9, 9.2 Hz, 1H), 2.70-2.62 (m, 1H), 2.54-2.46 (m, 1H), 2.42-2.35 (m, 1H), 2.30-2.22 (m, 1H), 2.15-2.10 (m, 1H), 1.95 (d, J=12.3 Hz, 1H), 1.84 (dd, J=13.8, 6.1 Hz, 1H), 1.61-1.53 (m, 1H), 1.52-1.42 (m, 1H), 1.35-1.29 (m, 1H); $^{13}$C NMR (125 MHz, CDCl$_3$) δ 211.1, 180.6, 174.3, 140.6, 133.0, 128.3, 124.3, 123.1, 109.3, 73.8, 69.9, 64.0, 60.4, 56.1, 51.6, 49.1, 40.4, 39.4, 36.5, 31.3, 26.7, 22.4; LCMS (ESI): m/z 399 [M+H]$^+$.

Example 4

It describes the process for the preparation of compounds of general formula VI, and the characterization data for the selected compounds of this class.

Compound of general formula V (0.1 mmol) was dissolved in THF:AcOH:water (0.4:0.4:0.4 mL) and NBS (0.1 mmol) was added slowly at −10° C. The reaction mixture was slowly warmed to room temperature and stirring continued for 2 h. After completion, the reaction mixture was quenched slowly with saturated sodiumbicarbonate solution at 0° C. Then, the reaction mixture was diluted with DCM (30 mL) and washed with water (2×20 mL). The organic layer was separated, dried over Na$_2$SO$_4$ and concentrated under vacuum. The crude was purified on flash chromatography, using EtOAc in hexane as an eluent to obtain the title compounds of general formula VI.

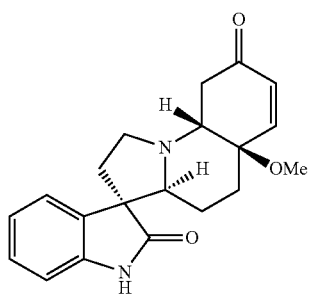

(3S,3a'S,5a'R,9a'R)-5a'-Methoxy-1',2',3a',4',5',5a'9',9a'-octahydro-8'H-spiro[indoline-3,3'-pyrrolo[1,2-a]quinoline]-2,8'-dione (1w): Off-white solid, 17 mg, 51% yield; mp: 213-215° C.; $R_f$=0.4 (silica gel, hexane/EtOAc 1:4); $^1$H NMR (500 MHz, Acetone-d$_6$): δ 9.35 (s, 1H), 7.39 (d, J=7.3 Hz, 1H), 7.18 (td, J=7.7, 1.1 Hz, 1H), 7.00 (t, J=7.5 Hz, 1H), 6.91 (d, J=7.7 Hz, 1H), 6.82 (d, J=10.3 Hz, 1H), 5.97 (d, J=10.3 Hz, 1H), 4.05-3.98 (m, 1H), 3.31 (s, 3H), 3.20-3.11 (m, 1H), 3.09-3.01 (m, 2H), 2.72 (d, J=8.8 Hz, 2H), 2.32-2.23 (m, 1H), 1.98-1.88 (m, 1H), 1.77-1.63 (m, 2H), 1.40-1.27 (m, 2H), 1.03-0.95 (m, 1H); $^{13}$C NMR (125 MHz, Acetone-d$_6$): δ 198.8, 180.4, 156.7, 142.3, 134.5, 131.2, 128.3, 125.9, 122.4, 109.9, 75.4, 62.4, 57.1, 55.1, 50.7, 46.9, 35.4, 33.4, 30.4, 21.3; HRMS (m/z): [M+H]$^+$ calcd. for C$_{20}$H$_{23}$N$_2$O$_3$, 339.1708, found 339.1715.

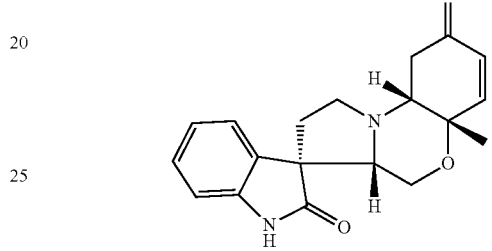

(3 S,3 aS,5aS,9aR)-5a-Methyl-1,2,3a,4,9,9a-hexahydrospiro[benzo[b]pyrrolo[1,2-d][1,4]oxazine-3,3'-indoline]-2',8(5aH)-dione (1x): Off-white solid, 17 mg, 52% yield; mp: 215-217° C.; $R_f$=0.45 (silica gel, hexane/EtOAc 1:4); $^1$H NMR (500 MHz, CD$_3$OD): δ 7.31 (d, J=7.4 Hz, 1H), 7.22 (t, J=7.7 Hz, 1H), 7.07 (t, J=7.5 Hz, 1H), 6.87 (d, J=7.7 Hz, 1H), 6.67 (d, J=10.8 Hz, 1H), 6.03 (d, J=10.8 Hz, 1H), 3.70 (t, J=10.5 Hz, 1H), 3.49 (t, J=8.3 Hz, 1H), 3.28 (dd, J=10.5, 2.5 Hz, 1H), 2.88-2.80 (m, 2H), 2.77 (t, J=9.1 Hz, 1H), 2.69 (dd, J=10.1, 2.2 Hz, 1H), 2.49 (dd, J=17.4, 8.5 Hz, 1H), 2.28 (dt, J=13.0, 9.0 Hz, 1H), 2.07-2.01 (m, 1H), 1.43 (s, 3H)$^{13}$C NMR (125 MHz, CD$_3$OD): δ 199.2, 181.9, 155.6, 142.6, 134.4, 130.9, 129.4, 124.1, 123.8, 110.6, 74.4, 72.6, 69.7, 64.8, 55.7, 52.7, 41.3, 35.4, 24.9; HRMS (m/z): [M+H]$^+$ calcd. for C$_{19}$H$_{21}$N$_2$O$_3$, 325.1552, found 325.1555.

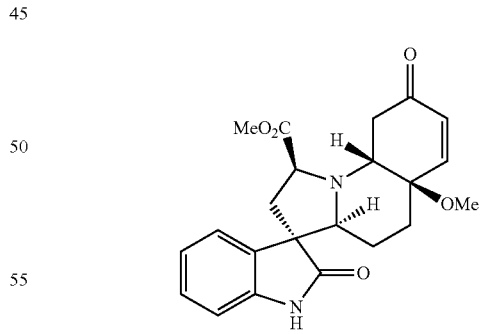

Methyl (1'S, 3 S,3a'S,5a'R,9a'R)-5a'-methoxy-2,8'-dioxo-1',2',3a',4',5a',8',9',9a'-octahydro-5H-spiro[indoline-3,3'-pyrrolo[1,2-d]quinoline]-1'-carboxylate (1y): Off-white solid, 19 mg, 48% yield; mp: 246-248° C.; $R_f$=0.4 (silica gel, hexane/EtOAc 1:4); [α]$_D$=−12.5 (0.002 M in acetone); $^1$H NMR (500 MHz, Acetone-d$_6$): δ 8.78 (s, 1H), 7.34 (d, J=7.3 Hz, 1H), 7.11 (td, J=7.7, 0.9 Hz, 1H), 6.95 (t, J=7.5 Hz, 1H), 6.80 (d, J=7.7 Hz, 1H), 6.52 (dd, J=10.2, 2.1 Hz, 1H), 6.08 (d, J=10.2 Hz, 1H), 4.07 (dd, J=9.0, 1.5 Hz, 1H), 3.74 (s, 3H), 3.44 (dd, J=10.1, 3.6 Hz, 1H), 3.27 (s, 3H), 3.20 (d, J=2.3 Hz, 1H), 3.03 (dd, J=16.4, 3.0 Hz, 1H), 2.56-2.49 (m, 1H), 2.12 (d, J=9.3 Hz, 1H), 1.46-1.25 (m, 3H); $^{13}$C NMR (125 MHz, Acetone-$d_6$): δ 197.9, 179.8, 173.8, 148.0, 141.4, 132.5, 132.1, 128.0, 123.8, 122.3, 109.1, 71.5, 69.0, 62.0, 60.5, 55.6, 51.3, 50.5, 38.4, 37.9, 32.2, 21.5. HRMS (m/z): [M+H]$^+$ calcd. for $C_{22}H_{25}N_2O_5$, 397.1763, found 397.1774.

Example 5

Study on Cellular and Mitochondrial Metabolic Functions

We examined the ability of compounds of the invention to enable the identification of chemotypes as potential inhibitors of mitochondrial functions. Such compounds would be useful not only as chemical probes targeting cellular energy metabolism but also as potential leads for the development of drugs targeting the mitochondrial function in cancer. Thus, the cellular mitochondrial activity was measured in Hepa1-6 cell line (CRL-1830, ATCC) after exposure to compounds of the invention for 24 h. These efforts identified compounds 1d and 1q as promising leads, which were found to deplete ATP production up to 60% and 50% (FIG. 1a), and reduce ΔΨm by 82% and 77%, respectively (FIG. 1b). The observed increase in redox potential (FIG. 1c), as a result of oxidative stress and accumulation of reducing equivalents, supports the idea of suppression and cellular stress response induction in Hepa1-6 cells due to the effect of compounds 1d and 1q. Additionally, the exposure of Hepa1-6 cells to 1d and 1q for 48 h resulted in a potent suppression of cells proliferation (FIG. 1d) without noticeable cytotoxic necrosis (FIG. 1e). Furthermore, compounds 1d and 1q were shown to diminish the proliferation of Hepa1-6 to different degrees with compound 1d being the most potent.

Since ATP is the main product of the mitochondria as the cells powerhouse, the decrease in ATP content indicated the ability of compounds 1d and 1q to interfere with the machinery of cellular energy metabolism. This was validated by a parallel inhibition of the ΔΨm with the maximum response observed at a concentration of 1 μM decreasing the normalized ΔΨm in the test system by 90% (1q), 82% (1d) (FIG. 1b). In addition, 1d and 1q strongly affected the redox potential to a point where the cells succumb to the induced stress (FIG. 1c). The inhibition of glycolysis and the consequent downregulation of ATP are utilized not only for targeting cancer cells but also to sensitize the resistant cancer cells to classical chemotherapies such as, doxorubicin, cisplatin and paclitaxel.

Example 6

Induced Proliferation Study

Figure 2:
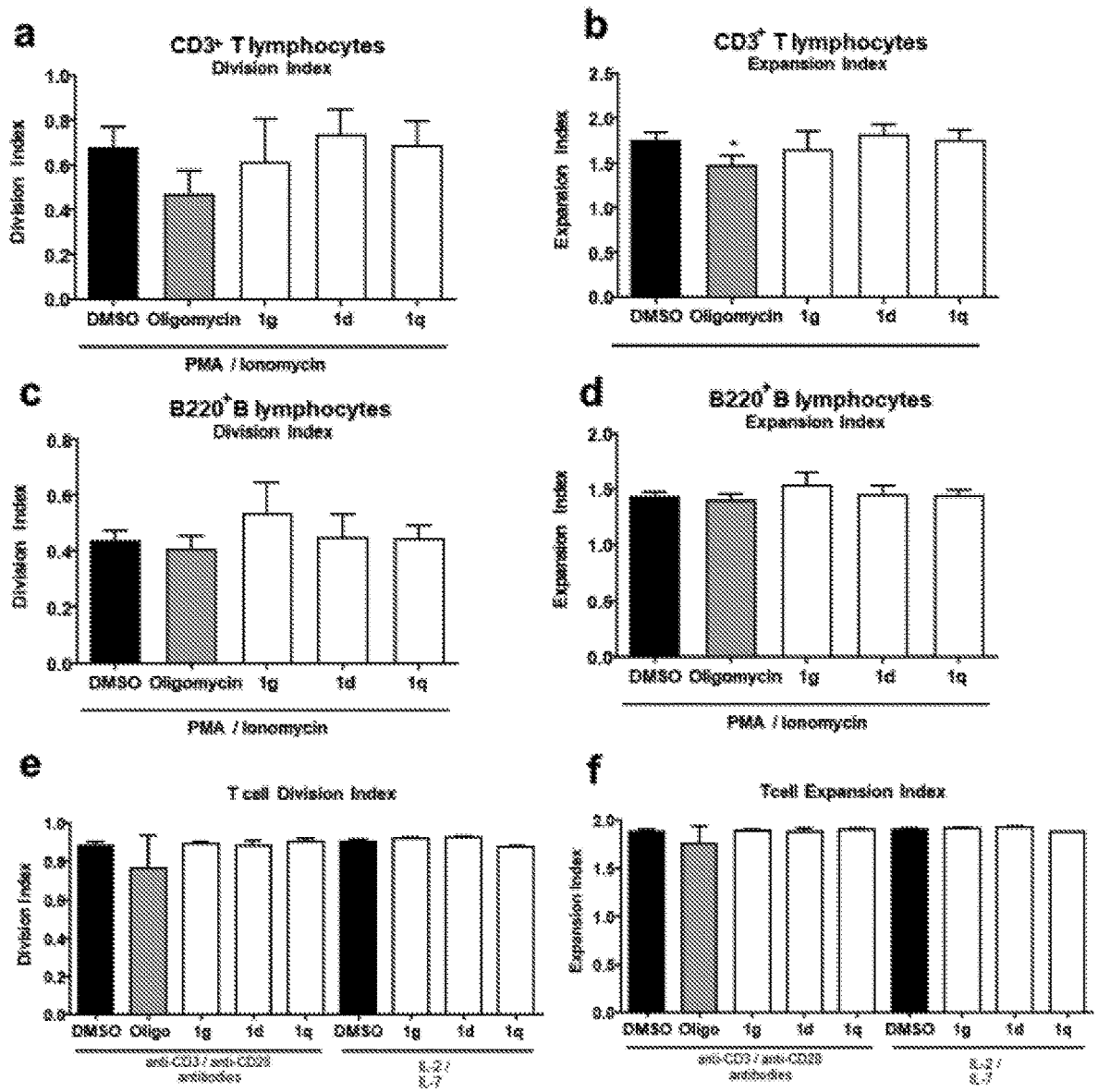
FIG. 2 Screening of a pilot library on cellular functions in Hepa1-6. a Effect of compounds 1d and 1q on immune cell proliferation in lymphocytes or isolated T cells. a-b Effect of compounds 1d and 1q on $CD3^+$ T lymphocytes. c-d Effect of compounds 1d and 1q on $B220^+$ B lymphocytes. e-f Effect of compounds 1d and 1q on isolated T cells. Error bars indicate standard deviation based on three replicated calculations. Significance was tested using an ANOVA test, with Dunnett's multiple comparison test. *$p<0.05$

After seeing the ability of compounds 1d and 1q to target mitochondrial machinery, we tested their effect on T- and B-cells activation and proliferation. Interestingly, compounds 1d and 1q did not suppress T- and B-cell function as indicated by the non-significant effects on the division indices (FIGS. 2a, 2c) or expansion indices (FIGS. 2b, 2d) of T- and B-cells upon stimulation using phorbol 12-myristate 13-acetate (PMA) (PMA)/Ionomycin. In addition, treatment of isolated T-cells with 1d and 1q did not significantly affect the activation-induced proliferation upon stimulation of T-cells with either anti-CD3/CD28 antibodies or cytokines IL-2/IL-7 (FIGS. 2e, 2f). Thus, while retaining the suppressive effect on the proliferation of the highly metabolically active Hepa1-6, these compounds did not suppress T- and B-cell activation. Thus, the overall impact of 1d and 1q on metabolism appears to be a driving force in the inhibition of cell proliferation. This inhibition of mitochondrial functions in cancer cells without altering the immunologic al activation or reprogramming of T- and B-cells, represents a promising strategy in cancer immunotherapy.

RELATED REFERENCES

U.S. Patent Documents

1. US20180044295A1, February 2018
2. U.S. Pat. No. 7,691,819B2, April 2010
3. U.S. Pat. No. 7,582,619B2, September 2009
4. US 20050272723A1, December 2005
5. U.S. Pat. No. 9,511,064 B2, December 2016

Foreign Patent Documents

1. EP0202774A3, November 1986
2. WO 2017/190038 A1, November 2017

Non-Patent Documents

1. Taleb et al., Multidirectional desymmetrization of pluripotent building block en route to diastereoselective synthesis of complex nature-inspired scaffolds. *Nat. Commun.* 2018, 4989.
2. Godfraind et al., Effects of yohimbine, rauwolscine and corynanthine on contractions and calcium fluxes induced by depolarization and prostaglandin F2α in rat aorta. *Br. J. Pharmac.* 1983, 80,115.
3. Deka et al., "Biochemical Studies and Virtual Screening of Phytochemical Reservoir from Northeastern Indian Plants to Identify Anti-Cancer Agents. *TBAP,* 2018, 8, 104.

The invention claimed is:
1. A novel compound of the formula I

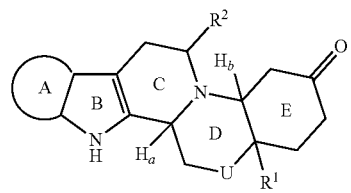

wherein,

denotes a phenyl ring which may be unsubstituted or substituted with 1, 2, 3 or 4 substituents independently selected from a halogen atom, CN, $R^3$, $OR^3$, $SR^3$, $N(R^3)_2$, $C(O)R^3$, $C(O)OR^3$, $NR^3C(O)R^3$, $C(O)NR^3$, $SO_2R^3$, $NR^3SO_2R^3$, or $SO_2N(R^3)_2$;

U denotes —CH$_2$ or —O;

$R^1$ denotes halogen atom, $R^3$, $OR^3$, $SR^3$, $N(R^3)_2$, $NR^3C(O)R^3$, $C(O)NR^3$, $SO_2R^3$, $NR^3SO_2R^3$, or $SO_2N(R^3)_2$; and $R^2$ denotes hydrogen, halogen atom, CN, $R^3$, $OR^3$, $SR^3$, $N(R^3)_2$, $C(O)R^3$, $C(O)OR^3$, $NR^3C(O)R^3$, $C(O)NR^3$, $SO_2R^3$, $NR^3SO_2R^3$, $SO_2N(R^3)_2$, $CH_2C(O)R^3$, $CH_2C(O)OR^3$, $CH_2NR^3C(O)R^3$, $CH_2C(O)NR^3$, $CH_2SO_2R^3$, $CH_2NR^3SO_2R^3$, or $CH_2SO_2N(R^3)_2$; and $R^3$ is independently hydrogen or an optionally substituted group selected from a $C_{1-6}$ aliphatic group, a monocyclic 3-8 membered saturated, partially unsaturated, or aryl ring having 0-4 heteroatoms independently selected from nitrogen, oxygen, or sulfur, or a bicyclic 8-10 membered saturated, partially unsaturated, or aryl ring having 0-5 heteroatoms independently selected from nitrogen, oxygen, or sulfur;

or a pharmaceutically acceptable salt thereof.

2. The compound of claim 1, wherein $H_a$, $H_b$, $R^1$ and $R^2$ are in the form of pure enantiomers, diastereoisomers or racemic mixtures.

3. The compound of claim 1, wherein $R^3$ is selected from the group consisting of: $-CX_3$, $-CHX_2$, and $-CH_2X$, wherein X is chlorine, fluorine, bromine, or iodine.

4. The compound of claim 1, wherein ring A is phenyl or a substituted phenyl.

5. A novel compound of the formula V

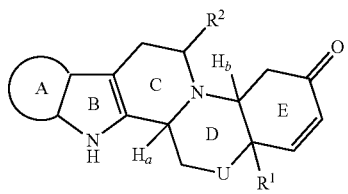

wherein

denotes a phenyl ring which may be unsubstituted or substituted with 1, 2, 3 or 4 substituents independently selected from a halogen atom, CN, $R^3$, $OR^3$, $SR^3$, $N(R^3)_2$, $C(O)R^3$, $C(O)OR^3$, $NR^3C(O)R^3$, $C(O)NR^3$, $SO_2R^3$, $NR^3SO_2R^3$, or $SO_2N(R^3)_2$;

U denotes $-CH_2$ or $-O$;

$R^1$ denotes halogen atom, $R^3$, $OR^3$, $SR^3$, $N(R^3)_2$, $NR^3C(O)R^3$, $C(O)NR^3$, $SO_2R^3$, $NR^3SO_2R^3$, or $SO_2N(R^3)_2$;

$R^2$ denotes hydrogen, halogen atom, CN, $R^3$, $OR^3$, $SR^3$, $N(R^3)_2$, $C(O)R^3$, $C(O)OR^3$, $NR^3C(O)R^3$, $C(O)NR^3$, $SO_2R^3$, $NR^3SO_2R^3$, $SO_2N(R^3)_2$, $CH_2C(O)R^3$, $CH_2C(O)OR^3$, $CH_2NR^3C(O)R^3$, $CH_2C(O)NR^3$, $CH_2SO_2R^3$, $CH_2NR^3SO_2R^3$, or $CH_2SO_2N(R^3)_2$; and $R^3$ is independently hydrogen or an optionally substituted group selected from a $C_{1-6}$ aliphatic group, a monocyclic 3-8 membered saturated, partially unsaturated, or aryl ring having 0-4 heteroatoms independently selected from nitrogen, oxygen, or sulfur, or a bicyclic 8-10 membered saturated, partially unsaturated, or aryl ring having 0-5 heteroatoms independently selected from nitrogen, oxygen, or sulfur;

or a pharmaceutically acceptable salt thereof.

6. A process for the preparation of the compound of formula V of claim 5, in which the process utilizes the below formulas III and IV as starting materials

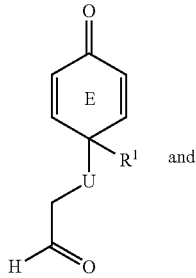

Formula III

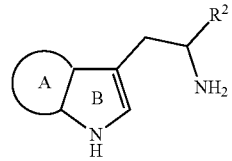

Formula IV wherein the process comprises the following steps in one-pot manner:
(i) Compound of formula III and IV are mixed in a suitable aprotic solvent at −100° C. to −20° C.,
(ii) Trifluroacetic acid is slowly added to the above mixture at −100° C. to −20° C. and the reaction mixture was is slowly warmed to room temperature over a period of 2 to 12 hours,
(iii) After completion, reaction mixture is diluted with the same solvent and washed with aqueous basic solution, and
(iv) The organic layer is collected and concentrated, wherein the obtained crude is purified by column chromatography or recrystallization or precipitation procedures.

7. The process of claim 6, wherein the mole ratio of compound of formula III to compound of formula IV is about 1:1 to about 1:2.

8. The process of claim 6, wherein the aprotic solvent is dichloromethane.

9. The process of claim 6, wherein the aqueous basic solution is saturated $NaHCO_3$ solution.

10. The process of claim 6, wherein the mobile phase used for the column chromatography is selected from EtOAc/hexane or MeOH/DCM.

11. The process of claim 6, wherein the solvent used for the recrystallization procedure is selected from EtOAc or MeOH.

12. The process of claim 6, wherein the combination of solvents used for the precipitation is selected from EtOAc/diethylether or EtOAc/hexane or DCM/hexane.

* * * * *